US008642638B2

(12) United States Patent
Chesworth et al.

(10) Patent No.: US 8,642,638 B2
(45) Date of Patent: *Feb. 4, 2014

(54) TREATMENT OF COGNITIVE DISORDERS WITH (R)-7-CHLORO-N-(QUINUCLIDIN-3-YL) BENZO[B]THIOPHENE-2-CARBOXAMIDE AND PHARMACEUTICALLY ACCEPTABLE SALTS THEREOF

(75) Inventors: Richard Chesworth, Boston, MA (US); Gideon Shapiro, Gainesville, FL (US); Gerhard Koenig, Newton, MA (US)

(73) Assignee: EnVivo Pharmaceuticals, Inc., Watertown, MA (US)

(*) Notice: Subject to any disclaimer, the term of this patent is extended or adjusted under 35 U.S.C. 154(b) by 55 days.

This patent is subject to a terminal disclaimer.

(21) Appl. No.: 13/129,782

(22) PCT Filed: Nov. 19, 2009

(86) PCT No.: PCT/US2009/065173
§ 371 (c)(1),
(2), (4) Date: Aug. 9, 2011

(87) PCT Pub. No.: WO2010/059844
PCT Pub. Date: May 27, 2010

(65) Prior Publication Data
US 2011/0288119 A1      Nov. 24, 2011

Related U.S. Application Data

(60) Provisional application No. 61/116,106, filed on Nov. 19, 2008.

(51) Int. Cl.
*A61K 31/403*      (2006.01)
*C07D 487/02*     (2006.01)

(52) U.S. Cl.
USPC .......................................... 514/412; 548/453

(58) Field of Classification Search
None
See application file for complete search history.

(56) References Cited

U.S. PATENT DOCUMENTS

| | | |
|---|---|---|
| 4,605,652 A | 8/1986 | Welstead, Jr. |
| 4,721,720 A | 1/1988 | Wootton et al. |
| 4,783,478 A | 11/1988 | Wootton et al. |
| 4,851,407 A | 7/1989 | Wootton et al. |
| 4,985,420 A | 1/1991 | Hamminga et al. |
| 5,069,904 A | 12/1991 | Masterson |
| 5,114,947 A | 5/1992 | Imondi |
| 5,122,528 A | 6/1992 | Imondi |
| 5,198,437 A | 3/1993 | Hamminga et al. |
| 5,561,149 A | 10/1996 | Azria et al. |
| 5,599,937 A | 2/1997 | Glas et al. |
| 5,656,638 A | 8/1997 | Gaeta et al. |
| 5,703,116 A | 12/1997 | Gaeta et al. |
| 5,760,062 A | 6/1998 | Gaeta et al. |
| 5,863,936 A | 1/1999 | Gaeta et al. |
| 5,902,814 A | 5/1999 | Gordon et al. |
| 5,977,144 A | 11/1999 | Meyer et al. |
| 6,051,581 A | 4/2000 | Gordon et al. |
| 6,232,319 B1 | 5/2001 | Marazano et al. |
| 6,277,870 B1 | 8/2001 | Gurley et al. |
| 6,358,941 B1 | 3/2002 | Snorrason et al. |
| 6,416,735 B1 | 7/2002 | Carroll et al. |
| 6,479,510 B2 | 11/2002 | Myers et al. |
| 6,492,385 B2 | 12/2002 | Myers et al. |
| 6,500,840 B2 | 12/2002 | Myers et al. |
| 6,569,865 B2 | 5/2003 | Eifion |
| 6,780,861 B2 | 8/2004 | Nozulak |
| 6,861,443 B2 | 3/2005 | Gurley et al. |
| 6,869,958 B2 | 3/2005 | Li |
| 6,875,606 B1 | 4/2005 | Leonard et al. |
| 6,908,927 B2 | 6/2005 | Galli et al. |
| 6,911,543 B2 | 6/2005 | Walker et al. |
| 6,943,184 B2 | 9/2005 | Goldstein et al. |
| 6,953,855 B2 | 10/2005 | Mazurov et al. |
| 6,964,961 B2 | 11/2005 | Luzzio et al. |
| 6,964,972 B2 | 11/2005 | Peters et al. |
| 6,987,106 B1 | 1/2006 | Gallet et al. |
| 6,995,167 B2 | 2/2006 | Loch, III et al. |
| 7,067,261 B2 | 6/2006 | Bencherif et al. |
| 7,067,515 B2 | 6/2006 | Wishka et al. |
| 7,196,096 B2 | 3/2007 | Loch, III et al. |
| 7,214,686 B2 | 5/2007 | Bencherif et al. |
| 7,256,288 B2 | 8/2007 | Hendrix et al. |
| 7,358,057 B2 | 4/2008 | Wang et al. |
| 7,579,362 B2 | 8/2009 | Feuerbach et al. |

(Continued)

FOREIGN PATENT DOCUMENTS

| | | |
|---|---|---|
| AU | 200145207 | 6/2001 |
| AU | 2002316828 | 10/2002 |

(Continued)

OTHER PUBLICATIONS

Acker, Brad A. et al., "Discovery of N-[(3R,5R)-1-azabicyclo[3.2.1]oct-3-yl]furo[2,3-c]pyridine-5-carboxamide as an agonist of the α7 nicotinic acetylcholine receptor: In vitro and in vivo activity," *Bioorganic & Medicinal Chemistry Letters*, 18:12 (Jun. 2008) 3611-3615.

Adler, et al., "Normalization of auditory physiology by cigarette smoking in schizophrenic patients," *Am J Psychiatry*, 150 (1993) 1856-1861.

Adler, et al., "Schizophrenia, sensory gating, and nicotinic receptors," *Schizophr Bull*, 24 (1998) 189-202.

Ahnallen, Christopher G. "The role of the α7 nicotinic receptor in cognitive processing of persons with schizophrenia," *Current Opinion Psychiatry*, 25:2 (Mar. 2012) 103-108.

(Continued)

*Primary Examiner* — Sreeni Padmanabhan
*Assistant Examiner* — Svetlana M Ivanova
(74) *Attorney, Agent, or Firm* — Jones Day (57) ABSTRACT

(R)-7-chloro-N-(quinuclidin-3-yl)benzo[b]thiophene-2-carboxamide has been found to have procognitive effects in humans at unexpectedly low doses. Thus, (R)-7-chloro-N-(quinuclidin-3-yl)benzo[b]thiophene-2-carboxamide and pharmaceutically acceptable salts thereof can be used at unexpectedly low doses improve cognition.

25 Claims, 3 Drawing Sheets

(56) References Cited

U.S. PATENT DOCUMENTS

| | | |
|---|---|---|
| 7,732,477 B2 | 6/2010 | Hendrix et al. |
| 7,767,193 B2 | 8/2010 | Mazurov et al. |
| 7,795,453 B2 | 9/2010 | Flessner et al. |
| 7,902,222 B2 | 3/2011 | Ji et al. |
| 7,935,815 B2 | 5/2011 | Kimura et al. |
| 7,964,607 B2 | 6/2011 | Verhoest et al. |
| 8,076,355 B2 | 12/2011 | Hendrix et al. |
| 8,084,462 B2 | 12/2011 | Mazurov et al. |
| 8,124,618 B2 | 2/2012 | Mazurov et al. |
| 8,124,619 B2 | 2/2012 | Mazurov et al. |
| 8,124,620 B2 | 2/2012 | Mazurov et al. |
| 2002/0052389 A1 | 5/2002 | Myers et al. |
| 2003/0092613 A1 | 5/2003 | Lee et al. |
| 2003/0119840 A1 | 6/2003 | Galli et al. |
| 2004/0019053 A1 | 1/2004 | Roark |
| 2004/0039045 A1 | 2/2004 | Schiemann et al. |
| 2004/0043983 A1 | 3/2004 | Li |
| 2004/0249150 A1 | 12/2004 | Piotrowski et al. |
| 2004/0254373 A1 | 12/2004 | Piotrowski et al. |
| 2004/0266757 A1 | 12/2004 | Galli et al. |
| 2005/0004128 A1 | 1/2005 | Galli et al. |
| 2005/0020599 A1 | 1/2005 | Galli et al. |
| 2005/0031651 A1 | 2/2005 | Gervais et al. |
| 2005/0032845 A1 | 2/2005 | Goldstein et al. |
| 2005/0107460 A1 | 5/2005 | Luithle et al. |
| 2005/0119249 A1 | 6/2005 | Buntinx |
| 2005/0119325 A1 | 6/2005 | Hendrix et al. |
| 2005/0154045 A1 | 7/2005 | Luithle et al. |
| 2005/0209236 A1 | 9/2005 | Hendrix et al. |
| 2005/0245504 A1 | 11/2005 | Corbett et al. |
| 2005/0245531 A1 | 11/2005 | Ji et al. |
| 2005/0250816 A1 | 11/2005 | Piotrowski et al. |
| 2006/0160835 A1 | 7/2006 | Bencherif et al. |
| 2006/0167002 A1 | 7/2006 | Feuerbach et al. |
| 2007/0037844 A1 | 2/2007 | Luithle et al. |
| 2009/0054446 A1 | 2/2009 | Feuerbach et al. |
| 2009/0088418 A1 | 4/2009 | Pfister et al. |
| 2009/0221555 A1 | 9/2009 | Ahmed et al. |
| 2010/0004162 A1 | 1/2010 | Heintz et al. |
| 2010/0130540 A1 | 5/2010 | Duggan |
| 2010/0190771 A1 | 7/2010 | Claffey et al. |
| 2010/0222378 A1 | 9/2010 | Hendrix et al. |
| 2010/0261752 A1 | 10/2010 | Beattie et al. |
| 2010/0324085 A1 | 12/2010 | Flessner et al. |
| 2011/0009619 A1 | 1/2011 | Kimura et al. |
| 2011/0021590 A1 | 1/2011 | Duggan |
| 2011/0065696 A1 | 3/2011 | Kimura et al. |
| 2011/0262442 A1 | 10/2011 | Hamilton et al. |
| 2011/0269764 A1 | 11/2011 | Cohen et al. |
| 2011/0274628 A1 | 11/2011 | Borschke |
| 2011/0305751 A1 | 12/2011 | Gaillard |
| 2012/0010148 A1 | 1/2012 | Gozes et al. |
| 2012/0046283 A1 | 2/2012 | Campbell et al. |
| 2012/0053171 A1 | 3/2012 | Kitazawa et al. |
| 2012/0058992 A1 | 3/2012 | Cohen et al. |
| 2012/0071483 A1 | 3/2012 | Cohen et al. |
| 2012/0202842 A1 | 8/2012 | Hendrix et al. |

FOREIGN PATENT DOCUMENTS

| | | |
|---|---|---|
| CA | 2317025 | 6/2000 |
| CA | 2393004 | 6/2001 |
| CA | 2393538 | 6/2001 |
| CA | 2460075 | 3/2003 |
| CA | 2475773 | 3/2003 |
| CA | 2464194 | 5/2003 |
| CA | 2465680 | 5/2003 |
| CA | 2466344 | 5/2003 |
| CA | 2466375 | 5/2003 |
| CA | 2476417 | 8/2003 |
| CA | 2476624 | 8/2003 |
| CA | 2476681 | 8/2003 |
| DE | 3724059 | 2/1988 |
| DE | 3740984 | 6/1989 |
| DE | 3810552 | 10/1989 |
| DE | 10044905 | 3/2002 |
| DE | 10156719 | 5/2003 |
| DE | 10162442 | 7/2003 |
| EP | 0322016 | 6/1989 |
| EP | 0327335 | 8/1989 |
| EP | 0353371 | 2/1990 |
| EP | 0405617 | 1/1991 |
| EP | 0485962 | 5/1992 |
| EP | 0512350 | 11/1992 |
| EP | 1022029 | 7/2000 |
| EP | 2002-030084 | 1/2002 |
| EP | 1219622 | 7/2002 |
| EP | 1231212 | 8/2002 |
| EP | 2277850 | 1/2011 |
| GB | 2208862 | 4/1989 |
| GB | 2231265 | 11/1990 |
| JP | 11080027 | 3/1999 |
| JP | 2002030084 | 1/2002 |
| JP | 2003081978 | 3/2003 |
| WO | WO 91/09593 | 7/1991 |
| WO | WO 93/15073 | 8/1993 |
| WO | WO 96/33186 | 10/1996 |
| WO | WO 97/30998 | 8/1997 |
| WO | WO 99/03859 | 1/1999 |
| WO | WO 99/45926 | 9/1999 |
| WO | WO 99/62505 | 12/1999 |
| WO | WO 00/10997 | 3/2000 |
| WO | WO 01/29034 | 4/2001 |
| WO | WO 01/32619 | 5/2001 |
| WO | WO 01/32620 | 5/2001 |
| WO | WO 01/32622 | 5/2001 |
| WO | WO 01/36417 | 5/2001 |
| WO | WO 01/55150 | 8/2001 |
| WO | WO 01/60821 | 8/2001 |
| WO | WO 01/66546 | 9/2001 |
| WO | WO 02/15662 | 2/2002 |
| WO | WO 02/16357 | 2/2002 |
| WO | WO 02/20016 | 3/2002 |
| WO | WO 02/44176 | 6/2002 |
| WO | WO 02/057275 | 7/2002 |
| WO | WO 02/085901 | 10/2002 |
| WO | WO 02/096912 | 12/2002 |
| WO | WO 02/100857 | 12/2002 |
| WO | WO 02/100858 | 12/2002 |
| WO | WO 03/018585 | 3/2003 |
| WO | WO 03/029252 | 4/2003 |
| WO | WO 03/037896 | 5/2003 |
| WO | WO 03/044019 | 5/2003 |
| WO | WO 03/044020 | 5/2003 |
| WO | WO 03/044024 | 5/2003 |
| WO | WO 03/051874 | 6/2003 |
| WO | WO 03/055878 | 7/2003 |
| WO | WO 03/072578 | 9/2003 |
| WO | WO 03/078430 | 9/2003 |
| WO | WO 03/078431 | 9/2003 |
| WO | 03/055878 | 10/2003 |
| WO | WO 03/087102 | 10/2003 |
| WO | WO 03/087103 | 10/2003 |
| WO | WO 03/087104 | 10/2003 |
| WO | WO 03/091694 | 11/2003 |
| WO | WO 03/093250 | 11/2003 |
| WO | WO 03/094830 | 11/2003 |
| WO | WO 03/094831 | 11/2003 |
| WO | WO 03/104227 | 12/2003 |
| WO | WO 2004/013137 | 2/2004 |
| WO | WO 2004/016608 | 2/2004 |
| WO | WO 2004/016616 | 2/2004 |
| WO | WO 2004/016617 | 2/2004 |
| WO | WO 2004/019943 | 3/2004 |
| WO | WO 2004/019947 | 3/2004 |
| WO | 2004/029050 | 4/2004 |
| WO | WO 2004/029050 | 4/2004 |
| WO | WO 2004/039321 | 5/2004 |
| WO | WO 2004/039815 | 5/2004 |
| WO | WO 2004/043960 | 5/2004 |
| WO | WO 2004/052348 | 6/2004 |
| WO | WO 2004/052461 | 6/2004 |
| WO | WO 2004/052889 | 6/2004 |

(56) References Cited

FOREIGN PATENT DOCUMENTS

| | | |
|---|---|---|
| WO | WO 2004/052894 | 6/2004 |
| WO | WO 2004/056744 | 7/2004 |
| WO | WO 2004/064836 | 8/2004 |
| WO | 2004/085433 | 10/2004 |
| WO | WO 2004/085433 | 10/2004 |
| WO | WO 2005/012299 | 2/2005 |
| WO | 2005/092890 | 10/2005 |
| WO | WO 2005/092890 | 10/2005 |
| WO | WO 2005/117890 | 12/2005 |
| WO | WO 2006/010008 | 1/2006 |
| WO | WO 2006/030031 | 3/2006 |
| WO | 2006/065233 | 6/2006 |
| WO | WO 2006/065233 | 6/2006 |
| WO | WO 2006/066879 | 6/2006 |
| WO | 2007/038367 | 4/2007 |
| WO | WO 2007/038367 | 4/2007 |
| WO | WO 2008/100867 | 8/2008 |
| WO | WO 2009/018505 | 2/2009 |
| WO | WO 2009/073788 | 6/2009 |
| WO | WO 2010/059844 | 5/2010 |
| WO | WO 2010/098488 | 9/2010 |
| WO | WO 2010/098495 | 9/2010 |
| WO | WO 2010/132423 | 11/2010 |
| WO | WO 2011/009097 | 1/2011 |
| WO | WO 2011/033018 | 3/2011 |
| WO | WO 2011/036167 | 3/2011 |
| WO | WO 2011/044264 | 4/2011 |
| WO | WO 2011/044535 | 4/2011 |
| WO | WO 2011/044537 | 4/2011 |
| WO | WO 2011/047432 | 4/2011 |
| WO | WO 2011/054759 | 5/2011 |
| WO | WO 2011/063415 | 5/2011 |
| WO | WO 2011/064288 | 6/2011 |
| WO | WO 2011/084368 | 7/2011 |
| WO | WO 2011/139811 | 11/2011 |
| WO | WO 2011/146511 | 11/2011 |
| WO | WO 2011/156640 | 12/2011 |
| WO | WO 2011/156646 | 12/2011 |
| WO | WO 2011/156775 | 12/2011 |
| WO | WO 2011/156780 | 12/2011 |
| WO | WO 2011/156786 | 12/2011 |
| WO | WO 2011/159945 | 12/2011 |

OTHER PUBLICATIONS

Anderson et al., "Tools for Purifying the Product: Column Chromatography, Crystallization and Reslurrying," *Practical Process Research and Development*, Academic Press, San Diego (Jan. 1, 2000) 223-247.

Araki, Hiroaki et al. "Neuronal nicotinic receptor and psychiatric disorders: Functional and behavioral effects of nicotine," *Japanese J Pharmacol*, 88 (2002) 133-138.

Arendash, Gary W. et al. "Improved learning and memory in aged rats with chronic administration of the nicotinic receptor agonist GTS-21," *Brain Research*, 674 (1995) 252-259.

Baldeweg, et al. "Nicotinic modulation of human auditory sensory memory: Evidence from mismatch negativity potentials," *Int J Psychophysiol*, 59 (2006) 49-58.

Banerjee, Carolin et al. "Cellular expression of α7 nicotinic acetylcholine receptor protein in the temporal cortex in Alzheimer's and Parkinson's Disease—A stereological approach," *Neurobiology of Disease*, 7 (2000) 666-672.

Bednar, Ivan et al. "Selective nicotinic receptor consequences in APP$_{SWE}$ transgenic mice," *Molecular Cell Neurosci*, 20 (2002) 354-365.

Belluardo, N. et al. "Neurotrophic effects of central nicotinic receptor activation," *J Neural Transmission* [Supplement], 60 (2000) 227-245.

Belluardo, Natale et al. "Central nicotinic receptors, neurotrophic factors and neuroprotection," *Behavioural Brain Res*, 113 (2000) 21-34.

Bhat, B. et al., "A Novel One-Step Synthesis of 2-Methoxycarbonyl-thieno[2,3-b]quinolines and 3-Hydroxy-2-methoxycarbonyl-2,3-dihydrothieno[2,3-b]-quinolines," *Synthesis* (Aug. 1984) 673-676.

Bitner, R. Scott et al. "In vivo pharmacological characterization of a novel selective α7 neuronal nicotinic acetylcholine receptor agonist ABT-107: Preclinical considerations in Alzheimer's disease," *J Pharmacol Exp Ther*, 334:3 (2010) 875-886.

Bitner, Robert S. et al. "Broad-spectrum efficacy across cognitive domains by α7 nicotinic acetylcholine receptor agonism correlates with activation of ERK1/2 and CREB phosphorylation pathways," *J Neurosci*, 27:39 (Sep. 26, 2007) 10578-10587.

Biton, Bruno et al. "SSR180711, a novel selective α7 nicotinic receptor partial agonist: (I) Binding and functional profile," *Neuropsychopharmacology*, 32 (2007) 1-16.

Bjugstad, Kimberly B. et al. "Long-term treatment with GTS-21 or nicotine enhances water maze performance in aged rats without affecting the density of nicotinic receptor subtypes in neocortex," *Drug Dev Research*, 39 (1996) 19-28.

Blokland, A. et al., "State-dependent impairment in object recognition after hippocampal NOS inhibition," *NeuroReport*, 8:18 (Dec. 1998) 4205-4208.

Bodnar, Alice et al. "Discovery and structure—activity relationship of quinuclidine benzamides as agonists of α7 nicotinic acetylcholine receptors," *J Med Chem*, 48 (2005) 905-908.

Boess et al., "Inhibition of phosphodiesterase 2 increases neuronal cGMP, synaptic plasticity and memory performance," *Neuropharmacology*, 47 (2004) 1081-1092.

Boess, Frank G. et al. "The novel α7 nicotinic acetylcholine receptor agonist N-[(3R)-1-azabicyclo[2.2.2]oct-3-yl]-7-[2-(methoxy)phenyl]-1-benzofuran-2-carboxamide improves working and recognition memory in rodents," *J Pharmacol Exp Ther*, 321:2 (2007) 716-725.

Bogdal, D. et al., "Microwave-Assisted Preparation of Benzo[b]furans under Solventless Phase-Transfer Catalytic Conditions," *Tetrahedron*, 56 (2000) 8769-8773.

Boutros, et al. "Test-retest reliability of the P50 mid-latency auditory evoked response," *Psychiatry Res*, 39 (1991) 181-192.

Bridges, A.J. et al., "Fluorine as an Ortho-Directing Group in Aromatic Metalation: A Two Step Preparation of Substituted Benzo[b]thiophene-2-carboxylates" *Tetrahedron Letters*, 33:49 (1992) 7499-7502.

Briggs, Clark A. et al. "Functional characterization of the novel neuronal nicotinic acetylcholine receptor ligand GTS-21 in vitro and in vivo," *Pharmacol Biochem Behavior*, 57:1/2 (1997) 231-241.

Brittain, H.G., ed., "Methods for the Characterization of Polymorphs and Solvates," *Polymorphism in Pharmaceutical Solids* (Jan. 1, 1999) 227-278.

Broide, R.S. et al., "The α7 Nicotinic Acetylcholine Receptor in Neuronal Plasticity," *Molecular Neurobiology*, vol. 20 (1999) 1-16.

Buccafusco et al., "Desensitization of Nicotinic Acetylcholine Receptors as a Strategy for Drug Development," *J of Pharm. and Exp. Ther.*, 328:2 (2009) 364-370.

Byrn, S. et al. "Pharmaceutical Solids: A Strategic Approach to Regulatory Considerations," *Pharmaceutical Research*, Kluwer Academic Publishers, New York, 12:7 (Jul. 1, 1995) 945-954.

Caira, M.R. "Crystalline Polymorphism of Organic Compounds," *Topics in Current Chemistry*, vol. 198 (Jan. 1, 1998) 163-208.

Chen, Y. et al. "Nicotine and an α7 selective nicotinic agonist AR-R17779 facilitate the induction of long-term potentiation induced by a short tetanus," *Soc Neuroscience*, Program No. 420.3 (Nov. 7, 2000). (Abstract only).

Krutcher, Keith A. "GTS-21" *Current Opinion in Central Peripheral Nervous System Investigational Drugs*, 2:4 (2000) 478-484.

Cummings, J. L. "Cholinesterase inhibitors: A new class of psychotropic compounds," *American Journal of Psychiatry*, 157:1 (Jan. 2000) 4-15.

D'Andrea, Michael R. et al. "Targeting intracellular Aβ42 for Alzheimer's Disease drug discovery," *Drug Dev Research*, 56 (2002) 194-200.

Dalebout, et al. "Reliability of the mismatch negativity in the responses of individual listeners," *J Am Acad Audiol*, 12 (2001) 245-253.

Dance, Amber et al. "The society for neuroscience 2009 meeting report, part 2," *J Alzheimers Disease*, 19 (2010) 1409-1415.

(56) References Cited

OTHER PUBLICATIONS

Davies, A.R.L. et al., "Characterisation of the binding of [$^3$H]methyllycaconitine: a new radioligand for labelling α7-type neuronal nicotinic acetylcholine receptors" *Neuropharmacology*, 38 (1999) 679-690.
De Bruin et al., "SLV330: A cannabinoid CB1 receptor antagonist, ameliorates deficits in the T-maze, object recognition and social recognition tasks in rodents," *Neurobiol Learn Mem*, 93 (2010) 522-531.
De Strooper, Bart et al. "The secretases: Enzymes with therapeutic potential in Alzheimer disease," *Nature Rev: Neurol*, 6 (Feb. 2010) 99-107.
De Wilde, et al., "A meta-analysis of P50 studies in patients with schizophrenia and relatives: differences in methodology between research groups," *Schizophr Res*, 97 (2007) 137-151.
Dierks, et al., "Event-related potentials and psychopharmacology: Cholinergic modulation of P300," *Pharmacopsychiatry*, 27 (1994) 72-74.
Dunbar, et al., "Effects of TC-1734 (AZD3480), a selective neuronal nicotinic receptor agonist, on cognitive performance and the EEG of young healthy male volunteers," *Psychopharmacology* (Berl), 191 (2007) 919-929.
Duncan et al., "Effects of smoking on acoustic startle and prepulse inhibition in humans," *Psychopharmacology* (Berl), 156 (2001) 266-272.
Easton, et al., "Beneficial effects of thiamine on recognition memory and P300 in abstinent cocaine-dependent patients," *Psychiatry Res*, 70 (1997) 165-174.
Ennaceur et al., "A new one-trial test for neurobiological studies of memory in rats. II: Effects of piracetam and pramiracetam," *Behav Brain Res*, 33 (1989) 197-207.
Ennaceur, A. et al., "A new one-trial test for neurobiological studies of memory in rats. 1: Behavioral data," *Behavioural Brain Research*, vol. 31 (1988) 47-59.
Ennaceur, A. et al., "Effects of physostigmine and scopolamine on rats' performances in object-recognition and radial-maze tests," *Psychopharmacology*, vol. 109 (1992) 321-330.
Feuerbach, D. et al. "The selective nicotinic acetylcholine receptor alpha7 agonist JN403 is active in animal models of cognition, sensory gating, epilepsy and pain," *Neuropharmacology*, 56:1 (Jan. 1, 2009) 254-263.
Folstein, Marshal et al., "'Mini-Mental State': A Practical Method for Grading the Cognitive State of Patients for the Clinician," *Journal of Psychiatric Research*, 12 (1975) 189-98.
Freedman et al., "Linkage disequilibrium for schizophrenia at the chromosome 15q13-14 locus of the α7-nicotinic acetylcholine receptor subunit gene (CHRNA7)," *Am J Med Genet*, 105 (2001) 20-22.
Freedman, Robert et al. "Initial phase 2 trial of a nicotinic agonist in schizophrenia," *Am J Psychiatry*, 165 (2008) 1040-1047.
Fuerst et al., "Range of sensory gating values and test-retest reliability in normal subjects," *Psychophysiology*, 44 (2007) 620-626.
Galasko, Douglas et al., "An Inventory to Assess Activities of Daily Living for Clinical Trials in Alzheimer's Disease," *Alzheimer Disease and Associated Disorders*, 11:S2 (1997) S33-S39.
Galzi, J.L. et al., "Neuronal Nicotinic Receptors: Molecular Organization and Regulations," *Neuropharmacology*, 34:6 (1995) 563-582.
George, Tony et al. "Nicotinic modulation of mesoprefrontal dopamine neurons: Pharmacologic and neuroanatomic characterization," *J Pharmacol Exp Ther*, 295:1 (2000) 58-66.
Gray, J.A. et al. "The pipeline and future of drug development in schizophrenia," *Molecular Psychiatry*, 12:10 (Oct. 2007) 904-922.
Gray, Richard et al. "Hippcampal synaptic transmission enhanced by low concentrations of nicotine," *Nature*, 383 (Oct. 1996) 713-716.
Guillory, J. K. "Generation of Polymorphs, Hydrates, Solvates and Amorphous Solids," *Polymorphism in Pharmaceutical Solids* (Jan. 1, 1999) 183-226.
Harwood, L. M. et al. "Experimental organic chemistry—Principles and Practice," *Experimental Chemistry—Organic Chemistry and Reaction* (Jan. 1, 1989) 127-132.

Hauser, T.A. et al. "TC-5619: An alpha7 neuronal nicotinic receptor-selective agonist that demonstrates efficacy in animal models of the positive and negative symptoms and cognitive dysfunction of schizophrenia," *Biochemical Pharmacology*, 78:7 (Oct. 1, 2009) 803-812.
Haydar, Simon N. et al. "Neuronal nicotinic acetylcholine receptors—Targets for the development of drugs to treat cognitive impairment associated with schizophrenia and Alzheimer's disease," *Curr Topics Med Chem*, 10 (2010) 144-152.
Heinrichs, R.W., "Meta-analysis and the science of schizophrenia: variant evidence or evidence of variants?" *Neurosci Biobehav Rev*, 28 (2004) 379-394.
Ho, Yuan-Soon et al. "The alpha-9 nicotinic acetylcholine receptor serves as a molecular target for breast cancer therapy," *J Exp Clin Med*, 3:6 (2011) 246-251.
Huang, Mei et al. "The alpha-7 receptor agonist EVP-6124 increases dopamine and glutamate efflux in rat medial prefrontal cortex and nucleus accumbens," *Biochem Pharmacol*, 82:2.13 (2011) 1040 (Abstract only).
Hughes, Charles P. et al., "A New Clinical Scale for the Staging of Dementia," *Brit. J. Psychiat.*, 140 (1982) 566-572.
Ishikawa, Masatomo et al. "α7 Nicotinic acetylcholine receptor as a potential therapeutic target for schizophrenia," *Curr Pharmaceut Design*, 17 (2011) 121-129.
Ji, Daoyun et al. "Timing and location of nicotinic activity enhances or depresses hippocampal synaptic plasticity," *Neuron*, 31 (Jul. 2001) 131-141.
Kaga et al., "Cat P300 and cholinergic septohippocampal neurons: depth recordings, lesions, and choline acetyltransferase immunohistochemistry," *Neurosci Res*, 13 (1992) 53-71.
Katada et al., "Long-term effects of donepezil on P300 auditory event-related potentials in patients with Alzheimer's disease," *J Geriatr Psychiatry Neurol*, 16 (2003) 39-43.
Kawamata, Jun et al. "Stimulating nicotinic receptors trigger multiple pathways attenuating cytotoxicity in models of Alzheimer's and Parkinson's diseases," *J Alzheimers Disease*, 24 (2011) 95-109.
Kem, William R. "The brain α7 nicotinic receptor may be an important therapeutic target for the treatment of Alzheimer's Disease: Studies with DMXBA (GTS-21)," *Behavioural Brain Res*, 113 (2000) 169-181.
Kem, William R. et al. "Hydroxy metabolites of the Alzheimer's drug candidate 3-[(2,4-dimethoxy)benzylidene]-anabaseine dihydrochloride (GTS-21): Their molecular properties, interactions with brain nicotinic receptors, and brain penetration," *Mol Pharmacol*, 65:1 (2004) 56-67.
Kitagawa, Harumi et al. "Safety, pharmacokinetics, and effects on cognitive function of multiple doses of GTS-21 in healthy male volunteers," *Neuropsychopharmacology*, 28 (2003) 542-551.
Koenig, G. et al. "EVP-6124, a novel and potent α7 nicotinic acetylcholine receptor agonist, improves memory acquisition, retention and retrieval and reverses scopolamine-induced memory deficits," *Soc Neuroscience*, Abst 887.6/FF136 (Oct. 21, 2009) 1-4.
Lanctôt, Krista L. et al. "Therapy for Alzheimer's disease: How effective are current treatments?" *Therapeut Adv Neurol Disorders*, 2:3 (2009) 163-180.
Levin, E. D. et al. "AR-R17779, an α7 nicotinic agonist, improves memory and learning in rats," *Behavioural Pharmacol*, 10 (1999) 675-780.
Levin, Edward D. et al. "Development of nicotinic drug therapy for cognitive disorders," *Euro J Pharmacol*, 393 (2000) 141-146.
Levin, Edward et al. "Nicotinic treatment for cognitive dysfunction," *Curr Drug Targets—CNS & Neurol Disord*, 1 (2002) 423-431.
Levin, Edward, "Nicotinic receptor subtypes and cognitive function," *J Neurobiology* 53 (2002) 633-640.
Li, X. D. et al. "Blood pressure and heart rate responses to central injection of choline: Role of α7-nicotinic cholinergic receptors," *Soc Neuroscience*, Program No. 136.6 (Nov. 3, 2002).(Abstract only).
Liu, Qing-song et al. "β-Amyloid peptide blocks the response of α7-containing nicotinic receptors on hippocampal neurons," *Proc Natl Acad Sci*, 98:8 (2001) 4734-4739.
Malysz, John et al. "In vitro pharmacological characterization of a novel selective α7 neuronal nicotinic acetylcholine receptor agonist ABT-107," *J Pharmacol Exp Ther*, 334:3 (2010) 863-874.

(56) References Cited

OTHER PUBLICATIONS

Mancuso, Cesare et al. "Pharmacologists and Alzheimer disease therapy: to boldly go where no scientist has gone before," *Expert Opin Invest Drugs*, 20:9 (2011) 1243-1261.

Mangialasche, Francesca et al. "Alzheimer's Disease: clinical trials and drug development," *Lancet Neurology*, 9 (2010) 702-716.

Maurer et al., "The relationship between the exposure and non-specific binding of thirty-three central nervous system drugs in mice," *Drug Metabolism and Disposition*, 33 (2005) 175-181.

Mazarov, Anatoly A. et al. "Discovery and development of α7 nicotinic acetylcholine receptor modulators," *J Med Chem*, 54 (2011) 7943-7961.

McGehee, D.S. et al., "Physiological Diversity of Nicotinic Acetylcholine Receptors Expressed by Vertebrate Neurons," *Annu. Rev. Physiol.*, vol. 57 (1995) 521-546.

Meyer, Edwin M. et al. "3[2,4-Dimethoxybenzylidene]anabaseine (DMXB) selectively activates rat α7 receptors and improves memory-related behaviors in a mecamylamine-sensitive manner," *Brain Research*, 768 (1997) 49-56.

Meyer, Edwin M. et al. "Analysis of 3-(4-hydroxy, 2-methoxybenzylidene)anabaseine selectivity and activity at human and rat α7 nicotinic receptors," *J Pharmacol Exp Ther*, 287 (1998) 918-925.

Meyer, Edwin M. et al. "Neuroprotective and memory-related actions of novel α7 nicotinic agents with different mixed agonist/antagonist properties," *J Pharmacol Exp Ther*, 284:3 (1998) 1026-1032.

Mimica, Ninoslav et al. "Current treatment options for people with Alzheimer's disease in Croatia," *Chemico-Biological Interactions*, 187 (2010) 409-410.

Mohs, Richard C. et al., "Development of Cognitive Instruments for Use in Clinical Trials of Antidementia Drugs: Additions to the Alzheimer's Disease Assessment Scale That Broaden Its Scope," *Alzheimer's Disease and Associated Disorders*, 11:S2 (1997) S13-S21.

Naatanen et al., "Generators of electrical and magnetic mismatch responses in humans," *Brain Topogr*, 7 (1995) 315-320.

Ng, Herman J. et al. "Nootropic α7 nicotinic receptor allosteric modulator derived from $GABA_A$ receptor modulators," *Proc Natl Acad Sci*, 104:19 (2007) 8059-8064.

Nishizaki, Tomoyuki et al. "Presynaptic nicotinic acetylcholine receptors as a functional target of Nefiracetam in inducing a long-lasting facilitation of hippocampal neurotransmission," *Alzheimer Disease Assoc Disord*, 14:Suppl 1 (2000) s82-s94.

Nishizaki, Tomoyuki et al. "The anti-dementia drug nefiracetam facilitates hippcampal synaptic transmission by functionally targeting presynaptic nicotinic ACh receptors," *Mol Brain Res*, 80 (2000) 53-62.

Nordberg et al., "Cholinesterase Inhibitors in the Treatment of Alzheimer's Disease," *Drug Safety*, 19:6 (Dec. 1998) 465-480.

Nordberg, Agneta "Neuroprotection in Alzheimer's Disease—New strategies for treatment," *Neurotoxicity Research*, 2 (2000) 157-165.

Numata, Atsushi, "1-Azabicycloalkane Compound and Pharmaceutical Use Thereof," *Patent Abstracts of Japan*, vol. 5 (May 3, 2002) and JP 2002 030084 (Jan. 29, 2002).

O'Neill, M.J. et al. "The role of neuronal nicotinic acetylcholine receptors in acute and chronic neurodegeneration," *Curr Drug Targets—CNS & Neurol Disord*, 1 (2002) 399-411.

Olincy et al., "Proof-of-concept trial of an alpha7 nicotinic agonist in schizophrenia," *Arch Gen Psychiatry*, 63 (2006) 630-638.

Papke, Roger L. et al. "Electrophysiological perspectives on the therapeutic use of nicotinic acetylcholine receptor partial agonists," *J Pharmacol Exp Ther*, 337:2 (2011) 367-379.

Papke, Roger L. et al. "α7 Receptor-selective agonists and modes of α7 receptor activation," *Euro J Pharmacol*, 393 (2000) 179-195.

Pichat, Philippe et al. "SSR180711, a novel selective α7 nicotinic receptor partial agonist: (II) Efficacy in experimental models predictive of activity against cognitive symptoms of schizophrenia," *Neuropsychopharmacology*, 32 (2007) 17-34.

Plath, Niels et al. "Can small molecules provide truly effective enhancement of cognition? Current achievements and future directions," *Expert Opin Invest Drugs*, 20:6 (2011) 795-811.

Potter et al., "Review of clinical correlates of P50 sensory gating abnormalities in patients with schizophrenia," *Schizophr Bull*, 32 (2006) 692-700.

Prickaerts et al., "Dissociable effects of acetylcholinesterase inhibitors and phosphodiesterase type 5 inhibitors on object recognition memory: acquisition versus consolidation," *Psychopharmacology*, 177 (2005) 381-390.

Prickaerts et al., "Phosphodiesterase type 5 inhibition improves early memory consolidation of object information," *Neurochem Int*, 45 (2004) 915-928.

Prickaerts, J. et al., "Possible role of nitric oxide-cyclic GMP pathway in object recognition memory: Effects of 7-nitroindazole and zaprinast", *European Journal of Pharmacology*, 337 (1997) 125-136.

Prickaerts, Jos et al. "EVP-6124, a novel and selective α7 nicotinic acetylcholine receptor partial agonist, improves memory performance by potentiating the acetylcholine response of α7 nicotinic acetylcholine receptors," *Neuropharmacology*, 62 (2012) 1099-1110.

Rezvani, A.H. et al., "Effect of R3487/MEM3454, a novel nicotinic alpha7 receptor partial agonist and 5-HT3 antagonist on sustained attention in rats," *Progress in Neuro-Psychopharmacology & Biological Psychiatry*, 33:2 (Mar. 17, 2009) 269-275.

Rezvani, Amir H. et al. "Cognitive effects of nicotine," *Biological Psychiatry*, 49 (2001) 258-267.

Rosen, Wilma G. et al., "A New Rating Scale for Alzheimer's Disease," *Am J Psychiatry*, 141:11 (Nov. 1984) 1356-1364.

Rosse, Richard B. et al. "Adjuvant Galantamine administration improves negative symptoms in a patient with treatment-refractory schizophrenia," *Clin Neuropharmacol*, 25 (2002) 272-275.

Sabbagh et al., "Drug development for Alzheimer's disease: Where are we now and where are we headed?" *American Journal of Geriatric Pharmacotherapy, Excerpta Medica*, 7:3 (Jun. 1, 2009) 167-185.

Sandman et al., "The auditory event-related potential is a stable and reliable measure in elderly subjects over a 3 year period," *Clin Neurophysiol*, 111 (2000) 1427-1437.

Schall et al., "Functional neuroanatomy of auditory mismatch processing: an event-related fMRI study of duration deviant oddballs," *Neuroimage*, 20 (2003) 729-736.

Seguela, P. et al., "Molecular Cloning, Functional Properties, and Distribution of Rat Brain α7: A Nicotinic Cation Channel Highly Permeable to Calcium," *Journal of Neuroscience*, 13:2 (Feb. 1993) 596-604.

Silva, Alcino J. et al. "Molecular and cellular mechanisms of cognitive function: Implications for psychiatric disorders," *Biological Psychiatry*, 47 (2000) 200-209.

Smulders, Chantal J.G.M. et al. "Cholinergic drugs potentiate human nicotinic α4β2 acetylcholine receptors by a competitive mechanism," *Euro J Pharmacol*, 509 (2005) 97-108.

Stahl, Stephen M., Ph.D. "Paying Attention to Your Acetylcholine, Part 2: The function of nicotinic receptors," *J Clin Psychiatry*, 61:9 (Sep. 2000) 628-629.

Strobel, Gabrielle "12th International Conference on Alzheimer's Disease (ICAD), Vienna, Austria," *J Alzheimers Disease*, 18 (2009) 973-990.

Sydserff, Simon et al. "Selective α7 nicotinic receptor activation by AZD0328 enhances cortical dopamine release and improves learning and attentional processes," *Biochem Pharmacol*, 78 (2009) 880-888.

Taly, Antoine et al. "Nicotinic receptors: Allosteric transitions and therapeutic targets in the nervous system," *Nature Rev: Drug Discovery*, 8 (Sep. 2009) 733-750.

Tcheremissine, Oleg V. et al. "Targeting cognitive deficits in schizophrenia: A review of the development of a new class of medicines from the perspective of community mental health researchers," *Expert Opin Invest Drugs*, 21:1 (2012) 7-14.

Thomsen, Morten S. et al. "Cognitive improvement by activation of α7 nicotinic acetylcholine receptors: From animal models to human pathophysiology," *Curr Pharmaceut Design*, 16 (2010) 323-343.

Townsend, Matthew "When will Alzheimer's Disease be cured? A pharmaceutical perspective," *J Alzheimers Disease*, 24 (2011) 43-52.

(56) References Cited

OTHER PUBLICATIONS

Trainor et al., "The importance of plasma protein binding in drug discovery," *Expert Opinion in Drug Discovery*, 20 (2007) 51-64.
Turetsky et al., "Neurophysiological endophenotypes of schizophrenia: the viability of selected candidate measures," *Schizophr Bull*, 33 (2007) 69-94.
Umbricht et al., "Mismatch negativity in schizophrenia: a meta-analysis," *Schizophr Res*, 76 (2005) 1-23.
Upadhyaya, Prerna et al. "Therapy of Alzheimer's Disease: An update," *African J Pharm Pharmacol*, 4:6 (Jun. 2010) 408-421.
Uteshev, V. V. et al. "Kinetic analysis of α7 nAChR fast desensitization in acutely dissociated neurons: Implications for therapeutics," *Soc Neuroscience*, Program No. 716.20 (Nov. 8, 2000).(Abstract only).
van Kampen, Marja et al. "AR-R17779 improves social recognition in rats by activation of nicotinic α7 receptors," *Psychopharmacology*, 172 (2004) 375-383.
Vaucher, E. et al. "Object recognition memory and cholinergic parameters in mice expressing human presenilin 1 transgenes," *Experimental Neurology*, 175 (2002) 398-406.
Vazquez, Raymond W. et al. "Identification of a new amino acid residue capable of modulating agonist efficacy at the homomeric nicotinic acetylcholine receptor, α7," *Molecular Pharmacol*, 55 (1999) 1-7.
Vippagunta, S.R. et al., "Crystalline Solids," *Advanced Drug Delivery Reviews*, 48 (2001) 3-26.
Wallace, T. L. et al., "R3487/MEM 3454, a novel nicotinic alpha 7 receptor partial agonist, improves attention and working memory performance in cynomolgus macaques," *Biochemical Pharmacology*, 78:7 (Oct. 1, 2009) 912.
Wallace, Tanya L. et al. "Drug targets for cognitive enhancement in neuropsychiatric disorders," *Pharmacol Biochem Behavior*, 99 (2011) 130-145.
Wallace, Tanya L. et al. "RG3487, a novel nicotinic α7 receptor partial agonist, improves cognition and sensorimotor gating in rodents," *J Pharmacol Exp Ther*, 336:1 (2011) 242-253.
Wallace, Tanya L. et al. "Targeting the nicotinic alpha7 acetylcholine receptor to enhance cognition in disease," *Biochem Pharmacol*, 82 (2011) 891-903.
Werber et al., "Evaluation of cholinergic treatment in demented patients by P300 evoked related potentials," *Neurol Neurochir Pol*, 35:Suppl 3 (2001) 37-43.
Werkheiser, J. L. et al. "Ultra-low exposure to alpha-7 nicotinic acetylcholine receptor partial agonists elicits an improvement in cognition that corresponds with an increase in alpha-7 receptor expression in rodents: Implications for low dose clinical efficacy," *Neuroscience*, 186 (2011) 76-87.
Wevers, A. et al. "Expression of nicotinic acetylcholine receptor subunits in the cerebral cortex in Alzheimer's disease: histotopographical correlation with amyloid plaques and hyperphosphorylated-tau protein," *Euro J Neuroscience*, 11 (1999) 2551-2565.
Whitehead et al., "Donepezil for the Symptomatic Treatment of Patients with Mild to Moderate Alzheimer's Disease: a Meta-Analysis of Individual Patient Data from Randomised Controlled Trials," *Int J Geriatr Psychiatry*, 19 (2004) 624-633.
Wirowski, D. et al. "Expression of α4 and α7 nicotinic receptor subunits in the temporal cortex in dementia with lewy bodies and controls," *Soc Neuroscience*, Program No. 195.18 (Nov. 11, 2001). (Abstract only).
Wishka, Donn G. et al., "Discovery of N-[(3R)-1-azabicyclo[2.2.2]oct-3-yl]furo[2,3-c]pyridine-5-carboxamide, an Agonist of the α7 Nicotinic Acetylcholine Receptor, for the Potential Treatment of Cognitive Deficits in Schizophrenia: Synthesis and Structure—Activity Relationship," *Journal of Medicinal Chemistry*, 49:14 (Jul. 2006) 4425-4436.
Woodruff-Pak, Diana "Preclinical experiments on cognition enhancement in Alzheimer's Disease: Drugs affecting nicotinic acetylcholine receptors," *Drug Dev Research*, 56 (2002) 335-346.

Acker et al., 'Discovery of N-[3r,5r)-1-azabicyclo[3.2.1]oct-3yl]furo-[2,3-]pyridine-f-carboxamide as an agonist of the alpha7 nicotinic acetylcholine receptor: In vitro and in vivo activity', Bioorg & Med Chem Lttrs, 12(2008), 3611-3615.
Adler et al., 'Normalization of auditory physiology by cigarette smoking in schizophrenic patients', Am J Psychiatry, 150(1993), 1856-1861.
Adler et al., 'Schizophrenia, sensory gating, and nicotinic receptors', Schizophr Bull, 24(1998), 189-202.
Baldeweg, et el. 'Nicotinic modulation of human auditory sensory memory: Evidence from mismatch negativity potentials' Int J Psychophysiol 59(2006), 49-58.
Boutros, et al. 'Test-retest reliability of the P50 mid-latency auditory evoked response', Psychiatry Res, 39(1991), 181-192.
Buccafusco et al., 'Desensitization of Nicotinic Acetylcholine Receptors as a Strategy for Drug Development', J of Pharm. and Exp. Ther., 328:2(2009), 364-370.
Dalebout, et al. 'Reliability of the mismatch negativity in the responses of individual listeners', J Am Acad Audiol, 12 (2001), 245-253.
de Wilde,et al., 'A meta-analysis of P50 studies in patients with schizophrenia and relatives: differences in methodology between research groups', Schizophr Res, 97(2007), 137-151.
Dierks, et al., 'Event-related potentials and psychopharmacology. Cholinergic modulation of P300', Pharmacopsychiatry, 27(1994), 72-74.
Dunbar, et al., 'Effects of TC-1734 (AZD3480), a selective neuronal nicotinic receptor agonist, on cognitive performance and the EEG of young healthy male volunteers', Psychopharmacology (Berl), 191(2007), 919-929.
Duncan et al., 'Effects of smoking on acoustic startle and prepulse inhibition in humans', Psychopharmacology (Berl), 156(2001), 266-272.
Easton, et al., 'Beneficial effects of thiamine on recognition memory and P300 in abstinent cocaine-dependent patients', Psychiatry Res, 70(1997), 165-174.
Freedman et al., 'Linkage disequilibrium for schizophrenia at the chromosome 15q13-14 locus of the alpha7-nicotinic acetylcholine receptor subunit gene (CHRNA7)' Am J Med Genet, 105(2001), 20-22.
Fuerst et al., 'Range of sensory gating values and test-retest reliability in normal subjects', Psychophysiology, 44 (2007), 620-626.
Gray et al., 'The pipeline and future of drug development in schizophrenia', Mol. Psych., 12(2007), 904-922.
Heinrichs, R.W., 'Meta-analysis and the science of schizophrenia: variant evidence or evidence of variants?' Neurosci Biobehav Rev, 28(2004.), 379-394.
Kaga et al., 'Cat 'P300' and cholinergic septohippocampal neurons: depth recordings, lesions, and choline acetyltransferase immunohistochemistry', Neurosci Res, 13(1992), 53-71.
Katada et al., 'Long-term effects of donepezil on P300 auditory event-related potentials in patients with Alzheimer's disease'.,. J Geriatr Psychiatry Neurol, 16(2003), 39-43.
Maurer et al., 'The relationship between the exposure and non-specific binding of thirty-three central nervous system drugs in mice', Drug Metabolism and Disposition, 33(2005), 175-181.
Naatanen et al., 'Generators of electrical and magnetic mismatch responses in humans', Brain Topogr, 7(1995), 315-320.
Olincy et al., 'Proof-of-concept trial of an alpha7 nicotinic agonist in schizophrenia', Arch Gen Psychiatry, 63(2006), 630-638.
Potter et al., 'Review of clinical correlates of P50 sensory gating abnormalities in patients with schizophrenia', Schizophr Bull, 32(2006), 692-700.
Sandman et al., 'The auditory event-related potential is a stable and reliable measure in elderly subjects over a 3 year period', Clin Neurophysiol, 111(2000), 1427-1437.
Schall et al., 'Functional neuroanatomy of auditory mismatch processing: an event-related fMRI study of duration-deviant oddballs', Neuroimage, 20(2003), 729-736.
Trainor et al., 'The importance of plasma protein binding in drug discovery', Expert Opinion in Drug Discovery, 20 (2003), 51-64.

(56) References Cited

OTHER PUBLICATIONS

Turetsky et al., 'Neurophysiological endophenotypes of schizophrenia: the viability of selected candidate measures', Schizophr Bull, 33(2007), 69-94.

Umbricht et al., 'Mismatch negativity in schizophrenia: a meta-analysis', Schizophr Res, 76(2005), 1-23.

Werber et al., 'Evaluation of cholinergic treatment in demented patients by P300 evoked related potentials', Neurol Neurochir Pol, 35 Suppl 3(2001), 37-43.

Wishka et al., 'Discover of of N-[(3r)-1-azabicyclo[2.2.2]oct-3-yl]furo-[2,3-c]pyridine-f-carboxamide an agonist of the alpha7 nicotinic acetylcholine receptor, for the potential treatment of cognitive deficits in schizophrenia: synthesis and structure—activity relationship', J. Med. Chem., 49(2006), 1125-4436.

International Search Report from corresponding PCT Application No. PCT/US2009/065173, mailed Mar. 23, 2010, (3 pgs).

Written Opinion from corresponding PCT Application No. PCT/US2009/065173, mailed Mar. 23, 2010, (5 pgs).

International Preliminary Report on Patentability from corresponding PCT Application No. PCT/US2009/065173, issued May 24, 2011, (6 pgs).

Cummings, "Cholinesterase inhibitors: A new class of psychotropic compounds" Am, J. of Psychiatry, 157(1), 2000, 4-15.

Boess et al., "Inhibition of phosphodiesterase 2 increases neuronal cGMP, synaptic plasticity and memory performance", Neuropharmacology 47(2004), 1081-1092.

Blokland et al., "State-dependent impairment in object recognition after hippocampal NOS inhibition", NeuroReport 9 (1998), 4205-4208.

Ennaceur, "A new one-trial test for neurobiological studies of memory in rats. 1: Behavioral data", Behav. Brain Res. 31(1988), 47-59.

Ennaceur, "Effects of physostigmine and scopolamine on rats' performances in object-recognition and radial-maze tests", Psychopharmacology 109(1992), 321-330.

Ennaceur et al., "A new one-trial test for neurobiological studies of memory in rats. II: Effects of piracetam and pramiracetam" Behav. Brain Res. 33(1989), 197-207.

De Bruin et al., "a cannabinoid CB1 receptor antagonist, ameliorates deficits in the T-maze, object recognition and social recognition tasks in rodents" Neurobiol. Learn. Mem. (In Press) SLV330.

Prickaerts et al. "Possible role of nitric oxide-cyclic GMP pathway in object recognition memory: Effects of 7-nitroindazole and zaprinast" Eur. J. Pharmacol. 337(1997), 125-136.

Prickaerts et al., "Phosphodiesterase type 5 inhibition improves early memory consolidation of object information" Neurochem Int. 45(2004), 915-928.

Prickaerts et al., "Dissociable effects of acetylcholinesterase inhibitors and phosphodiesterase type 5 inhibitors on object recognition memory: acquisition versus consolidation" Psychopharmacology 177(2005), 381-390.

Hauser et al. "TC-5619: An alpha7 neuronal nicotinic receptor-selective agonist that demonstrates efficacy in animal models of the positive and negative symptoms and cognitive dysfunction of schizophrenia", Biochemical Pharmacology, 78(7):803-812, 2009.

Baseline-adjusted average P50 gating ratio (T/C) as a function of group assignment [F=1.16, P=0.36]. The standard errors of each mean are noted in the legend. The bars left to right represent placebo, 0.3 mg test compound, and 1.0 mg test compound Baseline-adjusted average P50 difference (C-T) as a function of group assignment [F=3.97, P=0.07]. The standard errors of each mean are noted in the legend. The bars left to right represent placebo, 0.3 mg test compound, and 1.0 mg test compound

TREATMENT OF COGNITIVE DISORDERS WITH (R)-7-CHLORO-N-(QUINUCLIDIN-3-YL)BENZO[B]THIOPHENE-2-CARBOXAMIDE AND PHARMACEUTICALLY ACCEPTABLE SALTS THEREOF

This application is the U.S. national stage under 35 USC §371 of International Application Number PCT/US2009/065173, filed on Nov. 19, 2009, which claims priority to U.S. Application No. 61/116,106, filed on Nov. 19, 2008, the entire contents of which is hereby incorporated by reference.

BACKGROUND

Nicotinic acetylcholine receptors (nAChR) form a family of ion channels activated by acetylcholine. Functional receptors contain five subunits and there are numerous receptor subtypes. Studies have shown that central nicotinic acetylcholine receptors are involved in learning and memory. Nicotinic acetylcholine receptors of the alpha7 subtype are prevalent in the hippocampus and cerebral cortex.

WO 2003/055878 describes a variety of agonists of the alpha7 nAChR said to be useful for improving cognition. WO 2003/055878 suggests that certain agonists of the alpha7 nAChR are useful for improving perception, concentration, learning or memory, especially after cognitive impairments like those occurring for example in situations/diseases/syndromes such as mild cognitive impairment, age-associated learning and memory impairments, age-associated memory loss, Alzheimer's disease, schizophrenia and certain other cognitive disorders. Among the compounds described are (R)-7-chloro-N-(quinuclidin-3-yl)benzo[b]thiophene-2-carboxamide and pharmaceutically acceptable salts thereof.

SUMMARY

It has been found that (R)-7-chloro-N-(quinuclidin-3-yl)benzo[b]thiophene-2-carboxamide can have procognitive effects in humans at unexpectedly low doses. Thus, (R)-7-chloro-N-(quinuclidin-3-yl)benzo[b]thiophene-2-carboxamide and pharmaceutically acceptable salts thereof can be used at unexpectedly low doses improve cognition in individuals suffering from impaired cognition and in healthy individuals (i.e., individuals that are not suffering from an apparent cognitive deficit). For example, it can be used to improve cognition in patients suffering from Alzheimer's disease, schizophrenia and other disorders such as other neurodegenerative diseases (e.g., Huntington's Disease or Parkinson's Disease) and attention deficit disorder. It can be used treat certain disorders, e.g., Alzheimer's disease, schizophrenia (e.g., paranoid type, disorganized type, catatonic type, and undifferentiated type), schizophreniform disorder, schizoaffective disorder, delusional disorder, positive symptoms of schizophrenia, negative symptoms of schizophrenia at a daily dose of 3 mg, 2.70 mg, 2.50 mg, 2.25 mg, 2 mg, 1.75 mg, 1.50 mg, 1.25 mg, 1 mg, 0.7, 0.5, 0.3 mg or even 0.1 mg. The compound can be used to improve one or more aspects of cognition, e.g., one or more of: executive function, memory (e.g., working memory), social cognition, visual learning, verbal learning and speed of processing.

Described herein are methods for treating a patient by administering a pharmaceutical composition that comprises (R)-7-chloro-N-(quinuclidin-3-yl)benzo[b]thiophene-2-carboxamide or pharmaceutically acceptable salt thereof at a daily dose of: 3 mg, 2.70 mg, 2.50 mg, 2.25 mg, 2 mg, 1.75 mg, 1.50 mg, 1.25 mg, 1 mg, 0.7 mg, 0.5 mg, 0.3 mg, or 0.1 mg. The treatment can improve one or more facets of cognition (e.g., visual motor skill, learning, delayed memory, attention, working memory, visual learning, speed of processing, vigilance, verbal learning, visual motor function, social cognition, long term memory, executive function, etc.). The methods can be used to treat: Alzheimer's disease, schizophrenia (e.g., paranoid type, disorganized type, catatonic type, and undifferentiated type), schizophreniform disorder, schizoaffective disorder, delusional disorder, positive symptoms of schizophrenia or negative symptoms of schizophrenia.

"Dose" is the amount of active pharmaceutical ingredient (API) administered to a patient. For example 1 mg dose means 1 mg of API was administered to each patient each day.

"Active Pharmaceutical Ingredient" is defined as either (R)-7-chloro-N-(quinuclidin-3-yl)benzo[b]thiophene-2-carboxamide hydrochloride, (R)-7-chloro-N-(quinuclidin-3-yl)benzo[b]thiophene-2-carboxamide, (R)-7-chloro-N-(quinuclidin-3-yl)benzo[b]thiophene-2-carboxamide hydrochloride monohydrate or (R)-7-chloro-N-(quinuclidin-3-yl)benzo[b]thiophene-2-carboxamide hydrochloride solvate.

Where solvate represents a stoichiometric ratio of 0.1 to 10 molecules of solvent compared to (R)-7-chloro-N-(quinuclidin-3-yl)benzo[b]thiophene-2-carboxamide hydrochloride or (R)-7-chloro-N-(quinuclidin-3-yl)benzo [b]thiophene-2-carboxamide. Solvent molecules include but are not limited to water, methanol, 1,4 dioxane, ethanol, iso-propanol or acetone. In some cases water is the preferred solvate.

"The test compound" is defined as (R)-7-chloro-N-(quinuclidin-3-yl)benzo[b]thiophene-2-carboxamide hydrochloride.

"$EC_{ref}$" is the concentration of drug which elicits equal response in oocytes transfected with cloned human alpha7 receptor at 50 µM acetylcholine. Maximum stimulation of the cloned human alpha 7 receptor occurs at a concentration >250 µM of acetylcholine.

DETAILED DESCRIPTION

Described below are human clinical trials demonstrating that (R)-7-chloro-N-(quinuclidin-3-yl)benzo[b]thiophene-2-carboxamide elicits positive effects on cognition at an unexpectedly low daily dose of 1 mg or less. The positive effects are observed in both patients suffering from schizophrenia and in normal subjects. Also described below are studies showing that the free concentration of (R)-7-chloro-N-(quinuclidin-3-yl)benzo[b]thiophene-2-carboxamide in humans administered at daily 1 mg dose (of (R)-7-chloro-N-(quinuclidin-3-yl)benzo[b]thiophene-2-carboxamide hydrochloride) is at least a an order of magnitude lower than that expected to be required to exert a positive effect on cognitive function or can improve sensory electrophysiological responses which correlate with improved cognitive and functional performance in schizophrenia patients. Also described below are studies demonstrating that that (R)-7-chloro-N-(quinuclidin-3-yl)benzo[b]thiophene-2-carboxamide has an unexpectedly long half-life in humans compared to that expected based on pre-clinical studies in animals.

Because (R)-7-chloro-N-(quinuclidin-3-yl)benzo[b]thiophene-2-carboxamide can improve cognition at an unexpectedly low free plasma concentration, it is less likely to elicit harmful side-effects on its own and is less likely to exhibit harmful interactions with other drugs. Due to the unexpectedly low free plasma concentration required and the long half-life, (R)-7-chloro-N-(quinuclidin-3-yl)benzo[b]thiophene-2-carboxamide is expected to have special drug properties. These properties include a high margin of safety and a favorable dosing regimen (e.g., once daily dosing), both of which are highly advantageous for treating patients with cognitive defects as well as patients that are required to take additional medications.

Effect on Cognition in Schizophrenia Patients

The studies described below demonstrate that (R)-7-chloro-N-(quinuclidin-3-yl)benzo[b]thiophene-2-carboxamide hydrochloride can improve sensory electrophysiological responses which correlate with improved cognitive and functional performance in schizophrenia patients. These effects were observed at a daily dose as low as 0.3 mg.

Impairment of the ability of central nervous system to inhibit irrelevant sensory information has long been used as a model for understanding the deficits of attention seen in schizophrenic patients. Two approaches to the measurement of this ability have commonly been employed (see (Heinrichs, 2004; Potter et al., 2006; Turetsky et al., 2007; Umbricht and Krljes, 2005) for reviews and meta-analyses): (1) the sensory gating paradigm in which the presentation of one stimulus normally suppresses the response elicited by a stimulus which rapidly follows it. Schizophrenic patients typically exhibit less suppression (gating) of the second response. (2) the oddball or orienting paradigm in which a rare or unexpected event elicits a diminished response in schizophrenic patients because attentional resources are inappropriately focused on less salient aspects of the environment.

Two responses are commonly used assess brain activity: (1) the auditory P50 response elicited by the second member of a pair of clicks; and (2) the mismatch negativity (MMN) or N2 response evoked by a rarely occurring pure tone of no instructed relevance to the patient. Abnormalities in both P50 gating and the MMN have been reported in schizophrenic patients. Described below are studies assessing both of these responses in patients treated with (R)-7-chloro-N-(quinuclidin-3-yl)benzo[b]thiophene-2-carboxamide hydrochloride salt ("the test compound"). Also presented below are studies assessing the influence of the test compound on the N100 and P300 components of the evoked response. These components emerge after the P50 component and are as much related to attention to, and memory for, task relevant stimuli as to the neural processes by which task irrelevant stimuli are filtered (Turetsky et al., 2007; and Sandman and Patterson, 2000).

The neurobiology of P50 sensory gating is well documented in studies of human and animal subjects. Its regulation relies heavily on the integrity of the hippocampus and pathways that provide input to the hippocampus (Adler et al., 1998). For example, lesions of the cholinergic pathway originating in the medial septal nucleus disrupt the gating response, as do antagonists of low affinity nicotinic receptors. Cholinergic agonists, including nicotine itself (Adler et al., 1993; Duncan et al., 2001), have been shown to enhance P50 gating (Freedman et al., 2001; Olincy et al., 2006).

The neurobiology of the MMN is more complex. Imaging studies suggest that the primary and secondary auditory cortices in the temporal lobe are important for its generation (Naatanen and Alho, 1995). The dorsolateral prefrontal cortex also contributes (Schall et al., 2003). The neurotransmitter systems underlying the MMN are understudied and largely unknown. Yet, as is the case for P50, nicotinic cholinergic systems appear important (Baldeweg et al., 2006; Dunbar et al., 2007).

The sensitivity of P300 and N100 to cholinergic compounds has been known for many years (Dierks et al., 1994; Kaga et al., 1992). Various cholinergic antagonists—such as scopolamine—profoundly reduce the amplitudes of these components. In contrast, the components are markedly improved in amplitude by cholinesterase inhibitors (Katada et al., 2003; Werber et al., 2001) and other compounds that enhance cholinergic activity (Easton and Bauer, 1997).

The test described above were used to study the effect of the test compound on cognition in patients suffering from schizophrenia. Prior to testing the patient were dosed with: 1 mg of the test compound daily, 0.3 mg of the test compound daily or were administered a placebo for 20 days. Subjects were tested as described below.

P50 waves were elicited by clicks, 1 msec in duration, grouped in pairs in the classic S1-S2 sequence and presented through earpieces inserted into the auditory canals. Click intensity was adjusted individually to 50 dB above the hearing threshold. The offset-to-onset time from S1 to S2 was fixed at 500 msec. The offset-to-onset time between click pairs was varied from 7-11 sec. A total of 30 pairs of clicks were presented during each of 5 or more trial blocks with a one minute rest period interposed between each block.

EEG responses to the clicks were amplified to a gain of 10K and filtered (bandpass=3-30 Hz, 12 db roll-off). They were collected from 63 tin electrodes positioned by an electrode cap (Compumedics Neuroscan, Inc.). Additional electrodes of the same type were applied to the mid-forehead (ground) and in a vertical orientation above and below the left eye. Interelectrode impedances were maintained below 10 kOhms. All recordings were made with the subject sitting upright and relaxed but awake.

The EEG and eye movement signals were sampled by an analog-to-converter programmed to retain EEG activity from 50 msec preceding to 325 msec following click onset. The sampling rate was 1000 Hz. The digitized signals were stored in a database for subsequent analysis.

The 150 sweeps of S1 and S2 responses were screened and sweeps with voltage deviations greater than 100 microvolts in the eye movement channels were rejected. The remaining accepted sweeps were formed into time point averages. While blinded to group assignment, the investigator visually examined the evoked potential waveforms at the FCz electrode site. When possible, the investigator identified a negative trough immediately prior to the P50, the P50 itself, and the following N100 component. Admittedly, a distinct P50 component could not be visually identified in all patients at all time points. In those cases, the data were coded as missing.

P50 response amplitude was calculated as the voltage difference between the P50 peak and the preceding negative trough. The P50 gating ratio was then calculated after (Olincy et al., 2006) as the amplitude of the P50 response to the second (test) stimulus divided by the amplitude of the P50 response to the first (conditioning) stimulus. A small gating ratio is considered normal or optimal. The P50 amplitude difference (Fuerst et al., 2007) was also measured. It was the amplitude of the conditioning stimulus P50 response minus the amplitude of the test stimulus P50 response. A large P50 amplitude difference indicates normal gating.

N100 amplitude was calculated as the peak voltage of N100 minus the average voltage during the brief, 50 msec prestimulus period. As was the case for P50, N100 responses to the conditioning and test stimuli were calculated as ratios as well as differences.

The MMN and P300 components were elicited during the so-called oddball sequence. The stimulus sequence was a series of lower (500 Hz) and higher (1000 Hz) pitched pure tones presented at a rate of 1 tone per 0.6 sec. The tones were 50 msec in duration, 50 dB above hearing level, and randomly interspersed. The higher pitched tone was the oddball event. Across the series of 600 tones, it occurred at a probability of 0.2. The other tone occurred at the complementary probability of 0.8. Patients were instructed to ignore the tones and instead attend to a magazine held in the lap.

During the task, EEG and EOG activity were digitized at a rate of 500 Hz per channel for 50 msec preceding and 500 msec following stimulus onset. Trials contaminated by eyeblinks or eye movements were removed. An off-line program digitally filtered (bandpass=0.1-30 Hz, 12 db roll-off) responses to the rare and frequent events and constructed averaged event related responses for each electrode. At the FCz electrode, the MMN was measured by an automated algorithm that computed the summed amplitude, relative to the prestimulus baseline, over a 100-200 msec time window following the onsets of the rare (oddball) and frequent tones. MMN was then recalculated as the voltage difference between these responses. P300 amplitude was measured at the Pz electrode site as the peak amplitude between 250 and 500 msec following stimulus onset.

The plan for the analysis of the EEG measures was developed prior to breaking of the blind. It was based on the study design involving 3 groups (n=8 high dose, n=8 moderate dose, n=4 placebo) and 4 time points (1 predrug+3 postdrug). The plan offered several alternative strategies based upon the completeness and quality of the recordings. Unfortunately, in the case of the P50/N100 gating study, it was necessary to discard several patients and post-treatment assignment time points from the analysis because, in those instances, a P50 waveform was not identifiable and therefore could not be measured. This problem has been acknowledged in the literature but has not been discussed as openly and frequently as a skeptical scientist would like. For the analysis of P50 and N100, we adopted strategy 1b: "If many postdrug data points are missing/corrupted, then the remaining postdrug data points will be averaged together to create a single postdrug data point." The significant number of missing or unmeasurable P50's, unfortunately, removed another of our analysis options, wherein we hoped to focus on the subgroup of patients who showed the poorest sensory gating at baseline and might show the strongest improvement in gating after treatment. Of the 12 patients who provided valid and measurable P50 responses, 2 were in the placebo group, and 5 were in each of the two active dose groups.

Figure 1:
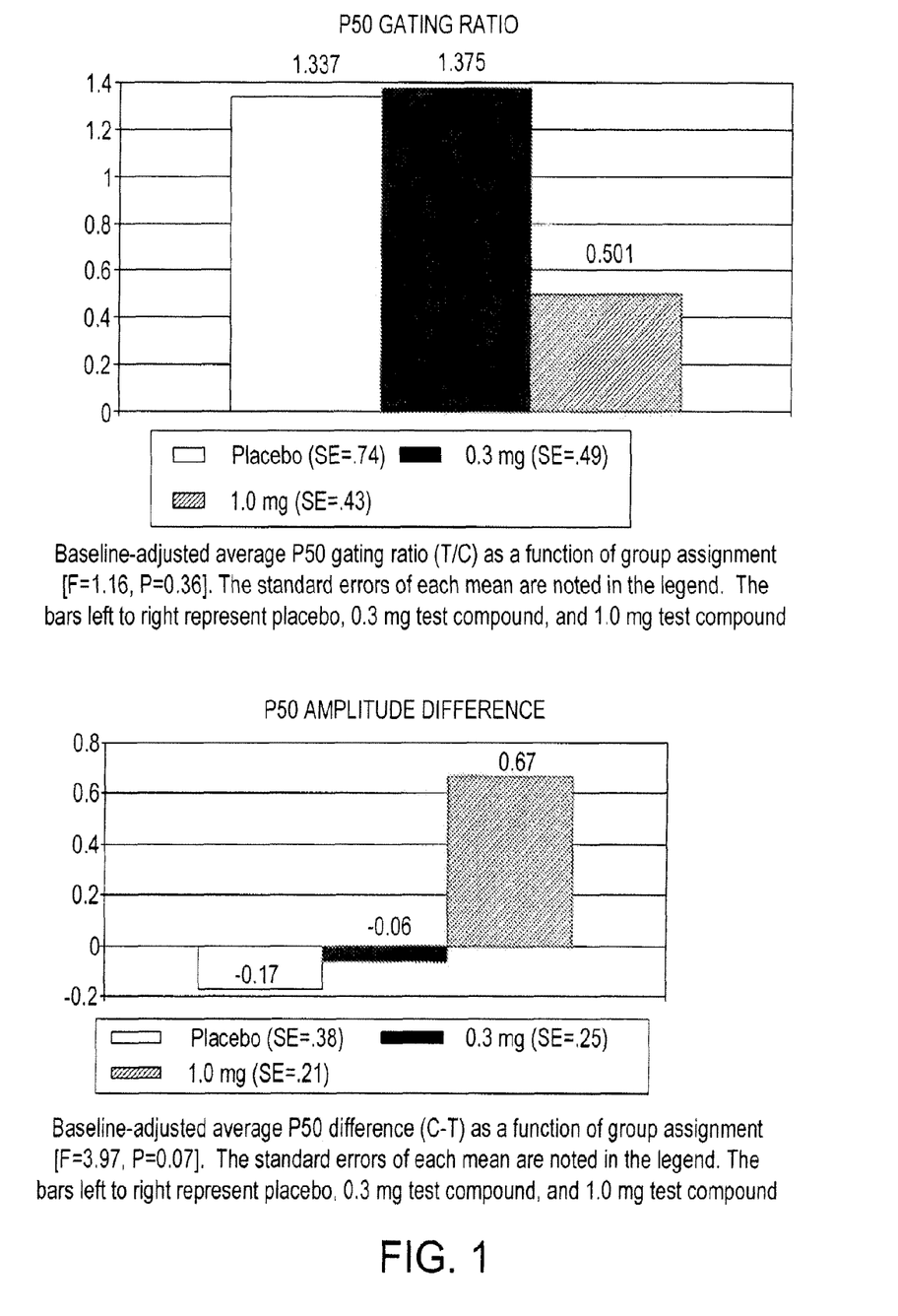
FIG. 1 depicts the results of a study on the effect of the test compound on P50 gating. The left panel depicts the baseline-adjusted average P50 gating ratio (T/C) as a function of group assignment [F=1.16, P=0.36]. The standard errors of each mean are noted in the legend. The bars (left to right) represent placebo, 0.3 mg test compound, and 1.0 mg test compound. The right panel depicts the baseline-adjusted average P50 difference (C–T) as a function of group assignment [F=3.97, P=0.07]. The standard errors of each mean are noted in the legend. The bars left to right represent placebo, 0.3 mg test compound, and 1.0 mg test compound.

FIG. 1 presents the results of simple analyses of covariance wherein all time points during the treatment period with valid data were averaged together to yield a single value. This value was then adjusted by regressing it against the baseline value and estimating a new value as if all patients possessed the same baseline. Then, a simple F test was performed. In support of the assumption of no significant differences between the treatment groups at the baseline (i.e., before treatment), we conducted simple ANOVAs evaluating the effect of treatment on all of the evoked potential components discussed presently. In no case did treatment significantly affect the baseline value. The left panel of FIG. 1 shows a non-significant [F=1.16, P=0.36] reduction (i.e., normalization) of the P50 gating ratio among patients receiving the 1.0 mg dose of the test compound. In contrast, the right panel of FIG. 1 shows the P50 amplitude difference score—a metric with superior reliability. It likewise shows normalization at the high dose. However, in this case, the change approaches statistical significance [F=3.97, P=0.07].

Figure 2:
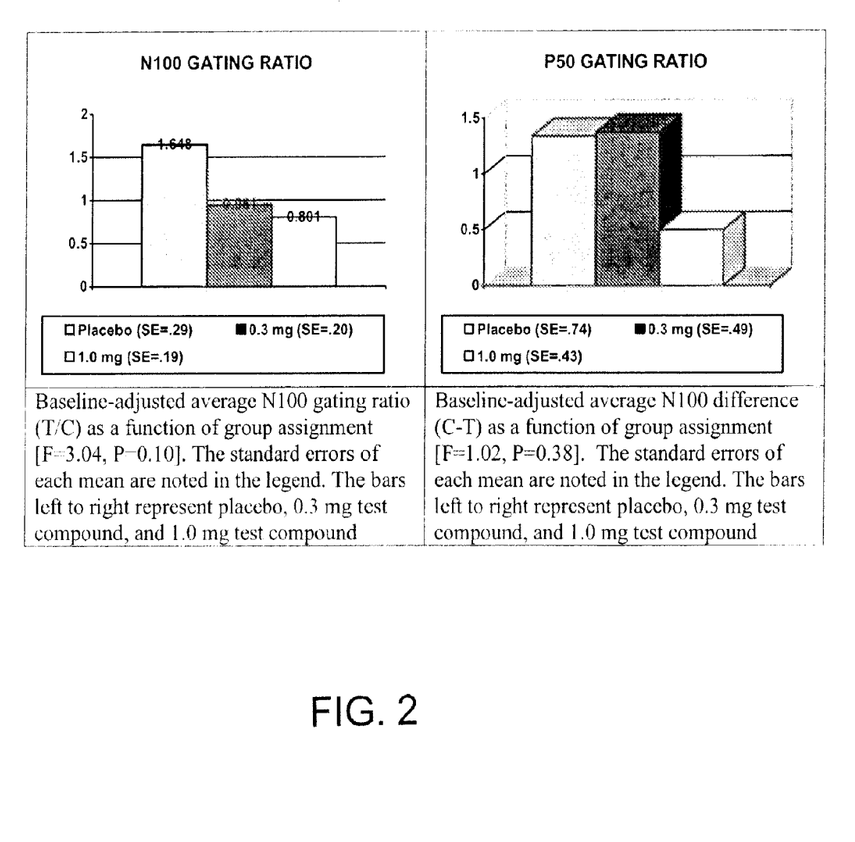
FIG. 2 depicts the results of a study on the effect of the test compound on P100 gating. The left panel depicts baseline-adjusted average N100 gating ratio (T/C) as a function of group assignment [F=3.04, P=0.10]. The standard errors of each mean are noted in the legend. The bars left to right represent placebo, 0.3 mg test compound, and 1.0 mg test compound The right panel depicts baseline-adjusted average N100 difference (C–T) as a function of group assignment [F=1.02, P=0.38]. The standard errors of each mean are noted in the legend. The bars left to right represent placebo, 0.3 mg test compound, and 1.0 mg test compound.

FIG. 2 presents an identical analysis of the N100 gating ratio and amplitude difference. Here, the gating ratio demonstrates a more reliable effect of the medication [F=3.04, P=0.10] than does the amplitude difference [F=1.02, P=0.38]. In the left panel of FIG. 2 normalization is suggested by a lower score. In the right panel of FIG. 2, normalization is indicated by the opposite direction of change.

MMN and P300 amplitude reflect activation of multiple precortical and cortical pathways sensitive to stimulus novelty, short term memory, and attention. MMN was calculated as the voltage difference over 100-200 msec post-stimulus onset between the responses to the rare and frequent stimuli. A more negative MMN suggests normal cognitive function. P300 is not entirely independent of MMN. P300 was calculated as the peak amplitude relative to the average voltage of the waveform during the 50 msec prestimulus period. A more positive P300 response is indicative of improved cognitive function. P300 is maximal in amplitude when the eliciting stimulus is both rare and task relevant (i.e., attended). In the present study, the rare stimulus was not task relevant. In fact, the patient was instructed to perform no task and to ignore the stimuli. In the present study, therefore, P300 amplitude is very small in comparison to amplitudes recorded under active task conditions. The present P300 component is more similar to the small, frontally-generated P300a described by Knight and colleagues than the large, parietally-generated P300b described in most studies of attentional dysfunction in schizophrenia.

In the analysis of P50 and N100 the baseline value was the covariate and all values obtained during the treatment period were averaged together. Data loss from unidentifiable MMN and P300 components was minimal. These analyses were conducted upon data obtained from n=4 patients treated with placebo, n=7 patients treated with 0.3 mg the test compound, and n=8 patients treated with 1.0 mg the test compound.

Figure 3:
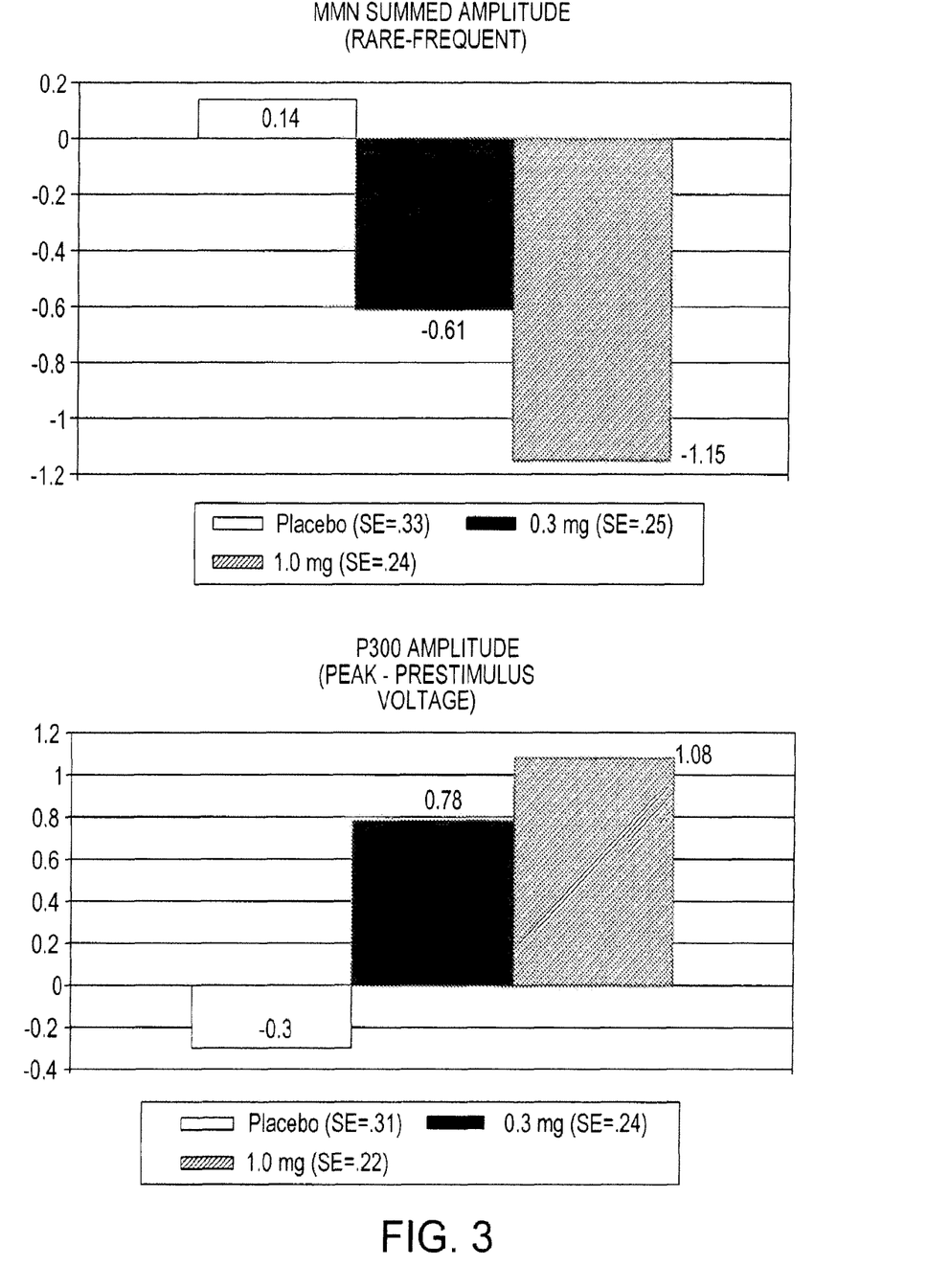
FIG. 3 depicts that results of a study on the effect of the test compound on MMN amplitude and P00 amplitude. The left panel depicts MMN as a function of group assignment [F=4.96, P=0.02]. The standard errors of each mean are noted in the legend. The bars left to right represent placebo, 0.3 mg test compound, and 1.0 mg test compound. The right panel depicts P300 amplitude (in microvolts relative to prestimulus voltage) measured at Pz scalp in response evoked by a rare but unattended stimulus. Group assignment effect: F=6.88, P=0.008. The standard errors of each mean are noted in the legend. The bars left to right represent placebo, 0.3 mg test compound, and 1.0 mg test compound.

FIG. 3 shows the results of the analysis of MMN and P300 amplitudes during the oddball task. Both evoked potential components were sensitive to the test compound in the predicted direction: MMN [F=4.96, P=0.02]; P300 [F=6.88, P=0.008]. In a dose-related manner, the test compound increased MMN and P300 amplitudes.

Despite the small number of patients enrolled in this trial, the analysis revealed several significant or marginally significant results. Both the 0.3 mg and 1.0 mg doses of the test compound evoked significantly (p<0.05) larger P300 and MMN components than were seen under the placebo condition. The effects of the test compound on an earlier component of the evoked response component (i.e., the P50) were limited to the highest, 1.0 mg, dose and were technically not significant (p=0.1). These results indicate that both the 0.3 mg dose and 1.0 mg dose of the test compound are anticipated to be effective in treating schizophrenia.

The relative sensitivity or insensitivity of various evoked response components to the test compound may be related to their size and reliability of measurement. In addition, sensitivity differences may relate to differences across the components in their neural generators and innervation by cholinergic afferents. Indeed, the two components (MMN and P300) which were most sensitive to the test compound are generated or modulated by frontal cortical pathways that receive input from brainstem cholinergic fibers. The P50 is, in contrast, generated subcortically.

Effect on Cognition in Normal Subjects

The impact of the test compound on cognition in normal subjects was assessed as described below. In these studies subjects were treated with the test compound dissolved in cranberry juice.

The impact of the test compound on cognition in normal subjects was assessed in a SAD (Single Ascending Dose) study with the Digit Symbol Substitution Test (DSST). Utilizing this test, the test compound was shown to have pro-cognitive effects at daily a dose as low as 1 mg. This is unexpected since acetylcholine esterase inhibitors, which indirectly activates the alpha 7 receptor by increasing acetylcholine levels, are not understood to exhibit pro-cognitive effects in normal subject and even in patients with cognitive impairment are not understood to exhibit pro-cognitive effects after a single dose. The positive effects of the test compound in the DSST indicate a beneficial effect on working memory and executive function.

In the MAD (Multiple Ascending Dose) studies cognition was assessed using tests from the CogState battery (cogstate.com). Utilizing this test, the test compound was shown to have pro-cognitive effects at daily a dose as low as 1 mg. The CogState battery is a proprietary computerized cognitive battery of tests measure various cognitive domains including: attention, identification capability, working memory, visual memory, and executive function. In these studies the test compound was found to have a positive impact on: visual motor skills, learning, executive function, and delayed memory. The profile of the response was unique insofar as the test compound had positive effects on non-verbal learning and memory and executive function without having a stimulatory effect on attention. The magnitude of the effects were, in many cases, significant with effect sizes being >0.4 (a threshold effect size which is commonly accepted as having clinical significance). This therapeutic profile (pro-cognitive effects on non-verbal learning and memory and executive function without a central stimulatory effect) indicates that the drug may be very beneficial in treating patients that have, as a feature of their condition, symptoms of anxiety or agitation.

(R)-7-chloro-N-(quinuclidin-3-yl)benzo[b]thiophene-2-carboxamide hydrochloride Shows Effects at Unexpectedly Low Dose and Free Plasma Concentration The studies described above demonstrate that (R)-7-chloro-N-(quinuclidin-3-yl)benzo[b]thiophene-2-carboxamide hydrochloride administered at a daily dose of 1.0 mg or 0.3 mg can improve cognition in patients suffering from schizophrenia and in normal subjects.

The fact that a 0.3 mg or 1.0 mg dose of (R)-7-chloro-N-(quinuclidin-3-yl)benzo[b]thiophene-2-carboxamide hydrochloride can elicit an effect in various measures of cognition is surprising because at these dosages the concentration of free drug is well below the Ki of the compound to bind to the alpha 7 receptor.

In order for a small molecule to exert action at its target, often a cell receptor, it must bind to its target. Thus, in general, a small molecule drug is expected to exhibit activity when the free drug concentration at the target (i.e., the concentration of drug that is free and available to bind to the target) approaches or exceeds the $K_i$ of the drug for target. Studies have shown that in numerous cases the free drug concentration in a particular tissue is about equal to the free drug concentration in plasma (Mauer et al. 2005 and Trainor 2007). For the brain, the free plasma concentration is generally considered to represent the maximum possible free drug concentration. The free drug concentration in plasma ($[\text{free drug}]_{plasma}$) is determined by measuring the total drug concentration in the plasma ($[\text{total drug}]_{plasma}$) and the free fraction of the drug, i.e., the fraction of the drug that is not bound to plasma protein ($fu_{plasma}$): $[\text{free drug}]_{plasma} = [\text{total drug}]_{plasma} \times fu_{plasma}$. The total plasma drug concentration and the fraction that binds to plasma protein can both be measured using techniques known to those of skill in the art.

Studies on (R)-7-chloro-N-(quinuclidin-3-yl)benzo[b]thiophene-2-carboxamide determined that the $EC_{ref}$ for human alpha7 receptor is approximately 0.158 μM and the $K_i$ (rat membrane) is approximately 10 nM. Additional studies found the following values for the free fraction of drug: Rat $fu_{plasma}$=0.112, Dog $fu_{plasma}$=0.107, Human $fu_{plasma}$=0.129.

Multiple ascending dose (MAD) human clinical trials were conducted. The maximum plasma concentration was determined and used to calculate the maximum free drug concentration which was used to determine the maximum free drug concentration as a fraction of the $EC_{ref}$ of the drug for human alpha7 receptor and the maximum free drug concentration as a fraction of the $K_i$ of the drug for rat brain alpha7 receptors. The $EC_{ref}$, the concentration of drug which elicits equal response in oocytes transfected with cloned human alpha7 receptor at 50 μM acetylcholine (the endogenous receptor ligand), was determined to be 0.158 μM. The $K_i$ for rat brain alpha7 receptors was determined to be 10 nM.

TABLE 1

| Study | Day | Dose | $C_{max}$ (ng/mL) | $C_{max}$ total (nM) | $C_{max}$ free (nM) | Fraction of α7 $EC_{ref}$ | Fraction of α7 Binding $K_i$ |
|---|---|---|---|---|---|---|---|
| SAD | 1 | 1 mg | 0.59 | 1.84 | 0.237 | 0.0015 | 0.0237 |
| SAD | 1 | 3.5 mg | 2.06 | 6.42 | 0.828 | 0.0052 | 0.0828 |
| MAD 1 | 1 | 1 mg | 0.63 | 1.96 | 0.252 | 0.0016 | 0.0252 |
| MAD 1 | 7 | 1 mg | 2.12 | 6.61 | 0.853 | 0.0054 | 0.0853 |
| MAD 1 | 14 | 1 mg | 2.64 | 8.23 | 1.06 | 0.0067 | 0.1060 |
| MAD 2 | 1 | 0.1 mg | 0.055 | 0.172 | 0.022 | 0.0001 | 0.0022 |
| MAD 2 | 21 | 0.1 mg | 0.232 | 0.724 | 0.093 | 0.0006 | 0.0093 |

TABLE 1-continued

| Study | Day | Dose | $C_{max}$ (ng/mL) | $C_{max}$ total (nM) | $C_{max}$ free (nM) | Fraction of α7 $EC_{ref}$ | Fraction of α7 Binding $K_i$ |
|---|---|---|---|---|---|---|---|
| MAD 2 | 1 | 1 mg | 0.623 | 1.943 | 0.251 | 0.0016 | 0.0251 |
| MAD 2 | 21 | 1 mg | 2.42 | 7.547 | 0.974 | 0.0062 | 0.0974 |
| MAD 3 | 1 | 0.3 mg | 0.182 | 0.568 | 0.073 | 0.0005 | 0.0073 |
| MAD 3 | 21 | 0.3 mg | 0.704 | 2.195 | 0.283 | 0.0018 | 0.0283 |
| MAD 3 | 1 | 1 mg | 0.547 | 1.71 | 0.221 | 0.0014 | 0.0221 |
| MAD 3 | 21 | 1 mg | 1.99 | 6.20 | 0.800 | 0.0051 | 0.0800 |

In human single and multiple ascending dose clinical trials in both healthy and schizophrenia patients a 0.3 mg daily dose and a 1.0 mg daily dose were shown to improve cognitive function or correlates of cognitive function. As can been seen from Table 1, which presents an analysis of the free drug concentration the 0.3 mg dose of (R)-7-chloro-N-(quinuclidin-3-yl)benzo[b]thiophene-2-carboxamide hydrochloride produces a maximum free plasma concentration of 0.073-0.283 nM which is 0.005 to 0.0018 of the α7 $EC_{ref}$ and 0.0073 to 0.0283 of the α7 $K_i$. These values are 35-2000 times lower than would have anticipated if efficacy was to be achieved when the free plasma concentration reached the $K_i$ or the $EC_{ref}$ concentrations. When a similar calculation is performed for the 1.0 mg doses (free plasma of 0.237-1.06 nM) these fractional values of the $K_i$ and $EC_{ref}$ concentrations are 0.0015 to 0.0067 ($EC_{ref}$) and 0.0237 to 0.106 (1($K_i$). These values are 9.4-667 times lower than expected.

Half-Life of (R)-7-chloro-N-(quinuclidin-3-yl)benzo[b]thiophene-2-carboxamide in Humans Table 2 presents half-life ($t_{1/2}$) data for (R)-7-chloro-N-(quinuclidin-3-yl)benzo[b]thiophene-2-carboxamide obtained from pre-clinical species as well as the half-life in humans determined in clinical trials.

TABLE 2

| Species | Route of administration | Dose | $t_{1/2}$ |
|---|---|---|---|
| Mouse | i.v. |  | n/a* |
| Rat | i.v. | 1 mg/kg | 2.77 h |
| Dog | i.v. | 0.5 mg/kg | 5.39 |
| Dog | i.v. | 3 mg/kg | 13 |
| Human | p.o. | 1 mg | 50.1-70.1 |

*(R)-7-chloro-N-(quinuclidin-3-yl)benzo[b]thiophene-2-carboxamide was unstable in mouse plasma and as such a half-life ($t_{1/2}$) could not be accurately calculated The half-life determined in rat and dog suggested a human half-life much shorter than the observed 60 hr half-life (initial allometric scaling suggested a half-life of about 8 hours). The unexpectedly long half-life in humans has several advantages. It allows for once a day dosing. The drug will also have a very small dynamic plasma range over the course of a day (about 15-20%). Thus, if a patient misses a daily dose, the plasma level and the consequent brain level will not be altered by a great degree. This means that the beneficial effects of the drug will be less dependent upon careful adherence to a specific dosing scheme. Third, long half-life and slow elimination also mean that the final dose will be lower than expected. This readily observed by looking at the $C_{max}$ values on Day 1 versus Day 21. The $C_{max}$ values on Day 21 are about 3.6-4.2 times higher than the Day 1 values. This ratio will translate into a dose that is 3.6-4.2 times lower than would normally be expected due to this favorable accumulation.

REFERENCES

Adler, L. E., Hoffer, L. D., Wiser, A., Freedman, R., 1993. Normalization of auditory physiology by cigarette smoking in schizophrenic patients. Am J Psychiatry 150, 1856-1861.

Adler, L. E., Olincy, A., Waldo, M., Harris, J. G., Griffith, J., Stevens, K., Flach, K., Nagamoto, H., Bickford, P., Leonard, S., Freedman, R., 1998. Schizophrenia, sensory gating, and nicotinic receptors. Schizophr Bull 24, 189-202.

Baldeweg, T., Wong, D., Stephan, K. E., 2006. Nicotinic modulation of human auditory sensory memory: Evidence from mismatch negativity potentials. Int J Psychophysiol 59, 49-58.

Boutros, N. N., Overall, J., Zouridakis, G., 1991. Test-retest reliability of the P50 mid-latency auditory evoked response. Psychiatry Res 39, 181-192.

Dalebout, S. D., Fox, L. G., 2001. Reliability of the mismatch negativity in the responses of individual listeners. J Am Acad Audiol 12, 245-253.

de Wilde, O. M., Bour, L. J., Dingemans, P. M., Koelman, J. H., Linszen, D. H., 2007. A meta-analysis of P50 studies in patients with schizophrenia and relatives: differences in methodology between research groups. Schizophr Res 97, 137-151.

Dierks, T., Frolich, L., Ihl, R., Maurer, K., 1994. Event-related potentials and psychopharmacology. Cholinergic modulation of P300. Pharmacopsychiatry 27, 72-74.

Dunbar, G., Boeijinga, P. H., Demazieres, A., Cisterni, C., Kuchibhatla, R., Wesnes, K., Luthringer, R., 2007. Effects of TC-1734 (AZD3480), a selective neuronal nicotinic receptor agonist, on cognitive performance and the EEG of young healthy male volunteers. Psychopharmacology (Berl) 191, 919-929.

Duncan, E., Madonick, S., Chakravorty, S., Parwani, A., Szilagyi, S., Efferen, T., Gonzenbach, S., Angrist, B., Rotrosen, J., 2001. Effects of smoking on acoustic startle and prepulse inhibition in humans. Psychopharmacology (Berl) 156, 266-272.

Easton, C. J., Bauer, L. O., 1997. Beneficial effects of thiamine on recognition memory and P300 in abstinent cocaine-dependent patients. Psychiatry Res 70, 165-174.

Freedman, R., Leonard, S., Gault, J. M., Hopkins, J., Cloninger, C. R., Kaufmann, C. A., Tsuang, M. T., Farone, S. V., Malaspina, D., Svrakic, D. M., Sanders, A., Gejman, P., 2001. Linkage disequilibrium for schizophrenia at the chromosome 15q13-14 locus of the alpha7-nicotinic acetylcholine receptor subunit gene (CHRNA7). Am J Med Genet 105, 20-22.

Fuerst, D. R., Gallinat, J., Boutros, N. N., 2007. Range of sensory gating values and test-retest reliability in normal subjects. Psychophysiology 44, 620-626.

Heinrichs, R. W., 2004. Meta-analysis and the science of schizophrenia: variant evidence or evidence of variants? Neurosci Biobehav Rev 28, 379-394.

Kaga, K., Harrison, J. B., Butcher, L. L., Woolf, N. J., Buchwald, J. S., 1992. Cat 'P300' and cholinergic septohippocampal neurons: depth recordings, lesions, and choline acetyltransferase immunohistochemistry. Neurosci Res 13, 53-71.

Katada, E., Sato, K., Sawaki, A., Dohi, Y., Ueda, R., Ojika, K., 2003. Long-term effects of donepezil on P300 auditory event-related potentials in patients with Alzheimer's disease. J Geriatr Psychiatry Neurol 16, 39-43.

Maurer, T., DeBartolo, D., Tess, D., and Scott, D., 2005. The relationship between the exposure and non-specific binding of thirty-three central nervous system drugs in mice. Drug Metabolism and Disposition 33, 175-181.

Naatanen, R., Alho, K., 1995. Generators of electrical and magnetic mismatch responses in humans. Brain Topogr 7, 315-320.

Olincy, A., Harris, J. G., Johnson, L. L., Pender, V., Kongs, S., Allensworth, D., Ellis, J., Zerbe, G. O., Leonard, S., Stevens, K. E., Stevens, J. O., Martin, L., Adler, L. E., Soti, F., Kem, W. R., Freedman, R., 2006. Proof-of-concept trial of an alpha7 nicotinic agonist in schizophrenia. Arch Gen Psychiatry 63, 630-638.

Potter, D., Summerfelt, A., Gold, J., Buchanan, R. W., 2006. Review of clinical correlates of P50 sensory gating abnormalities in patients with schizophrenia. Schizophr Bull 32, 692-700.

Sandman, C. A., Patterson, J. V., 2000. The auditory event-related potential is a stable and reliable measure in elderly subjects over a 3 year period. Clin Neurophysiol 111, 1427-1437.

Schall, U., Johnston, P., Todd, J., Ward, P. B., Michie, P. T., 2003. Functional neuroanatomy of auditory mismatch processing: an event-related fMRI study of duration-deviant oddballs. Neuroimage 20, 729-736.

Trainor, G, 2007. The importance of plasma protein binding in drug discovery. Expert Opinion in Drug Discovery 2:51-64.

Turetsky, B. I., Calkins, M. E., Light, G. A., Olincy, A., Radant, A. D., Swerdlow, N. R., 2007. Neurophysiological endophenotypes of schizophrenia: the viability of selected candidate measures. Schizophr Bull 33, 69-94.

Umbricht, D., Krljes, S., 2005. Mismatch negativity in schizophrenia: a meta-analysis. Schizophr Res 76, 1-23.

Werber, A. E., Klein, C., Rabey, J. M., 2001. Evaluation of cholinergic treatment in demented patients by P300 evoked related potentials. Neurol Neurochir Pol 35 Suppl 3, 37-43.

What is claimed is:

1. A method of improving cognition in a patient suffering from Schizophrenia, comprising:
    administering to said patient a daily dose in the range of between 0.1 mg to 3.0 mg of (R)-7-chloro-N-(quinuclidin-3-yl)benzo[b]thiophene-2-carboxamide, or a pharmaceutically acceptable salt thereof.

2. The method of claim 1, wherein the pharmaceutically acceptable salt of the (R)-7-chloro-N-(quinuclidin-3-yl)benzo[b]thiophene-2-carboxamide is: (R)-7-chloro-N-(quinuclidin-3-yl)benzo[b]thiophene-2-carboxamide hydrochloride; (R)-7-chloro-N-(quinuclidin-3-yl)benzo[b]thiophene-2-carboxamide hydrochloride monohydrate; or (R)-7-chloro-N-(quinuclidin-3-yl)benzo[b]thiophene-2-carboxamide hydrochloride solvate.

3. The method of claim 2, wherein the pharmaceutically acceptable salt of the (R)-7-chloro-N-(quinuclidin-3-yl)benzo[b]thiophene-2-carboxamide is administered to the patient.

4. The method of claim 3, wherein the pharmaceutically acceptable salt of the (R)-7-chloro-N-(quinuclidin-3-yl)benzo[b]thiophene-2-carboxamide is (R)-7-chloro-N-(quinuclidin-3-yl)benzo[b]thiophene-2-carboxamide hydrochloride.

5. The method of claim 3, wherein the pharmaceutically acceptable salt of the (R)-7-chloro-N-(quinuclidin-3-yl)benzo[b]thiophene-2-carboxamide is (R)-7-chloro-N-(quinuclidin-3-yl)benzo[b]thiophene-2-carboxamide hydrochloride monohydrate.

6. The method of claim 5, wherein the daily dose is in the range of between 0.3 mg to 1.5 mg.

7. The method of claim 5, wherein the daily dose is in the range of between 0.7 mg to 1.25 mg.

8. The method of claim 5, wherein the daily dose is in the range of between 1.0 mg to 3.0 mg.

9. The method of claim 5, wherein the daily dose is in the range of between 1.5 mg to 2.5 mg.

10. The method of claim 5, wherein the daily dose is in the range of between 1.75 mg to 2.25 mg.

11. The method of claim 5, wherein the daily dose is in the range of between 2.0 mg to 3.0 mg.

12. The method of claim 1, wherein the schizophrenia comprises a paranoid type, a disorganized type, catatonic type, or an undifferentiated type.

13. The method of claim 12, wherein the (R)-7-chloro-N-(quinuclidin-3-yl)benzo[b]thiophene-2-carboxamide, or pharmaceutically acceptable salt thereof, is administered as a pharmaceutical composition.

14. A method of improving cognition in a patient suffering from Alzheimer's disease, comprising:
    administering to said patient a daily dose in the range of between 0.1 mg to 3.0 mg of (R)-7-chloro-N-(quinuclidin-3-yl)benzo[b]thiophene-2-carboxamide, or a pharmaceutically acceptable salt thereof.

15. The method of claim 14, wherein the pharmaceutically acceptable salt of the (R)-7-chloro-N-(quinuclidin-3-yl)benzo[b]thiophene-2-carboxamide is: (R)-7-chloro-N-(quinuclidin-3-yl)benzo[b]thiophene-2-carboxamide hydrochloride; (R)-7-chloro-N-(quinuclidin-3-yl)benzo[b]thiophene-2-carboxamide hydrochloride monohydrate; or (R)-7-chloro-N-(quinuclidin-3-yl)benzo[b]thiophene-2-carboxamide hydrochloride solvate.

16. The method of claim 15, wherein the pharmaceutically acceptable salt of the (R)-7-chloro-N-(quinuclidin-3-yl)benzo[b]thiophene-2-carboxamide is administered to said patient.

17. The method of claim 16, wherein the pharmaceutically acceptable salt of the (R)-7-chloro-N-(quinuclidin-3-yl)benzo[b]thiophene-2-carboxamide is (R)-7-chloro-N-(quinuclidin-3-yl)benzo[b]thiophene-2-carboxamide hydrochloride.

18. The method of claim 16, wherein the pharmaceutically acceptable salt of the (R)-7-chloro-N-(quinuclidin-3-yl)benzo[b]thiophene-2-carboxamide is (R)-7-chloro-N-(quinuclidin-3-yl)benzo[b]thiophene-2-carboxamide hydrochloride monohydrate.

19. The method of claim 18, wherein the daily dose is in the range of between 0.3 mg to 1.5 mg.

20. The method of claim 18, wherein the daily dose is in the range of between 0.7 mg to 1.25 mg.

21. The method of claim 18, wherein the daily dose is in the range of between 1.0 mg to 3.0 mg.

22. The method of claim 18, wherein the daily dose is in the range of between 1.5 mg to 2.5 mg.

23. The method of claim 18, wherein the daily dose is in the range of between 1.75 mg to 2.25 mg.

24. The method of claim 18, wherein the daily dose is in the range of between 2.0 mg to 3.0 mg.

25. The method of claim 14, wherein the (R)-7-chloro-N-(quinuclidin-3-yl)benzo[b]thiophene-2-carboxamide, or pharmaceutically acceptable salt thereof, is administered as a pharmaceutical composition.

* * * * *